(12) United States Patent
Whitcomb

(10) Patent No.: US 10,174,377 B2
(45) Date of Patent: Jan. 8, 2019

(54) METHOD FOR DIAGNOSING AND ASSESSING RISK OF PANCREATITIS USING GENETIC VARIANTS

(71) Applicant: University Of Pittsburgh—Of The Commonwealth System Of Higher Education, Pittsburgh, PA (US)

(72) Inventor: David C. Whitcomb, Pittsburgh, PA (US)

(73) Assignee: University Of Pittsburgh—Of The Commonwealth System Of Higher Education, Pittsburgh, PA (US)

(*) Notice: Subject to any disclaimer, the term of this patent is extended or adjusted under 35 U.S.C. 154(b) by 0 days.

(21) Appl. No.: 14/707,515

(22) Filed: May 8, 2015

(65) Prior Publication Data

US 2015/0315649 A1  Nov. 5, 2015

Related U.S. Application Data

(63) Continuation of application No. PCT/US2013/069676, filed on Nov. 12, 2013.

(60) Provisional application No. 61/724,568, filed on Nov. 9, 2012.

(51) Int. Cl.

| | |
|---|---|
| *C12Q 1/68* | (2018.01) |
| *C12P 19/34* | (2006.01) |
| *C12Q 1/6883* | (2018.01) |
| *A61B 8/08* | (2006.01) |
| *A61B 6/03* | (2006.01) |
| *A61B 5/055* | (2006.01) |
| *A61B 1/273* | (2006.01) |
| *A61B 5/00* | (2006.01) |
| *A61M 5/00* | (2006.01) |
| *A61B 17/00* | (2006.01) |
| *A61M 27/00* | (2006.01) |

(52) U.S. Cl.
CPC ............ *C12Q 1/6883* (2013.01); *A61B 1/273* (2013.01); *A61B 5/055* (2013.01); *A61B 5/425* (2013.01); *A61B 6/032* (2013.01); *A61B 8/08* (2013.01); *A61B 17/00234* (2013.01); *A61M 5/00* (2013.01); *A61M 27/00* (2013.01); *C12Q 2535/131* (2013.01); *C12Q 2600/156* (2013.01); *C12Q 2600/172* (2013.01)

(58) Field of Classification Search
CPC . A61B 5/425; C12Q 1/6883; C12Q 2600/156
See application file for complete search history.

(56) References Cited

PUBLICATIONS

Zill P. et al. Molecular Psychiatry (2004) 9, 1030-1036.*
Wall J. D. et al. Nature Reviews—Genetics (Aug. 2003) vol. 4, 587-597.*
Pal P. et al. The Prostate 69:1548-1556 (2009).*
Hollegaard M. V. et al. BMC Genetics 2011 12:58, pp. 1-7.*
Derikx M.H.M. et al. Best Practice & Research Clinical Gastroenterology, vol. 24, Issue 3, Jun. 2010, pp. 251-270, Chronic Pancreatitis.*
Lozano-Leon, A. et al. "Duplication of a 303 kb Locus Containing PRSS1 and PRSS2 is Associated With Hereditary Pancreatitis in a Spanish Kindred" Gastroenterology, May 2011, vol. 140, Issue 5, Supplement 1, p. S-857.*
LaRusch et al., "The Common Chymotrypsinogen C (CTRC) Variant G60G (C.180T) Increases Risk of Chronic Pancreatitis But Not Recurrent Acute Pancreatitis in a North American Population," Clin Transl Gastroenterol, 6:e68 (2015).
Lozano-Leon et al., "Ductal adenocarcinoma of the pancreas: Expression of growth factor receptors, oncogenes and suppressor genes, and their relationship to pathological features, staging and survival," Oneol Lett. 2:161-166 (2011).
Masson et al., "PRSS1 copy number variants and promoter polymorphisms in pancreatitis: common pathogenetic mechanism, different genetic effects," Gut 2017.
Amasheh et al., "Claudin-2 expression induces cation-selective channels in tight junctions of epithelial cells," Journal of Cell Science 115:4969-4976 (2002).
Ammann et al., "Course and Outcome of Chronic Pancreatitis. Longitudinal Study of a Mixed Medical-Surgical Series of 245 Patients," Gastroenterology 86:820-828 (1984).
Angelow et al., "Biology of claudins," Am J of Physiol Renal Physiol 295:F867-876 (2008).
Applebaum-Shapiro et al., "Hereditary Pancreatitis in North America: The Pittsburgh-Midwest Multi-Center Pancreatic Study Group Study," Pancreatology 1:439-443 (2001).
Aung et al., "Differential expression of claudin-2 in normal human tissues and gastrointestinal carcinomas," Virchows Arch 448:428-434 (2006).
Bacanu et al., "The Power of Genomic Control," Am. J. of Hum. Genet. 66:1933-1944 (2000).
Brand et al., "Serum Biomarker Panels for the Detection of Pancreatic Cancer," Clin Cancer Res 17(4):805-816 (2011).
Burnette, ""Western blotting": Electrophoretic Transfer of Proteins from Sodium Dodecyl Sulfate—Polyacrylamide Gels to Unmodified Nitrocellulose and Radiographic Detection with Antibody and Radioiodinated Protein A," Analytical Biochemistry 112:195-203 (1981).
Chen et al., "Chronic Pancreatitis: Genetics and Pathogenesis," Annu. Rev. Genomics Hum. Genet. 10:63-87 (2009).
Clayton, "Sex chromosomes and genetic association studies," Genome Medicine 1:110 (2009).

(Continued)

*Primary Examiner* — Stephen T Kapushoc
(74) *Attorney, Agent, or Firm* — Baker Botts L.L.P.

(57) ABSTRACT

The present application discloses methods for predicting the risk of developing, or the presence of, recurrent acute pancreatitis and/or chronic pancreatitis, in a subject, by identifying the presence of an rs12688220 T allele, an rs7057398 T allele, and/or an rs10273639 C allele in a sample from the subject. The present application also discloses methods for treating or preventing pancreatitis in a human subject in need thereof.

7 Claims, 14 Drawing Sheets

Specification includes a Sequence Listing.

(56) References Cited

PUBLICATIONS

Dawra et al., "Intra-acinar Trypsinogen Activation Mediates Early Stages of Pancreatic Injury but Not Inflammation in Mice With Acute Pancreatitis," Gastroenterology 141:2210-2217 (2011).

Etemad et al., "Chronic Pancreatitis: Diagnosis, Classification, and New Genetic Developments," Gastroenterology 120:682-707 (2001).

Gorry et al., "Mutations in the Cationic Trypsinogen Gene are Associated with Recurrent Acute and Chronic Pancreatitis," Gastroenterology 113:1063-1068 (1997).

Hamza et al., "Genome-Wide Gene-Environment Study Identifies Glutamate Receptor Gene GRIN2A as a Parkinson's Disease Modifier Gene via Interaction with Coffee," PLoS Genet 7(8):e1002237 (2011).

International Search Report and Written Opinion dated Feb. 6, 2014 in International Application No. PCT/US2013/069676.

Irving et al., "Alcohol as a Risk Factor for Pancreatitis. A Systematic Review and Meta-Analysis," JOP. J Pancreas (Online) 10(4):387-392 (2009).

Johnson et al., "SNAP: a web-based tool for identification and annotation of proxy SNPs using HapMap," Bioinformatics 24(24):2938-2939 (2008).

Klei et al., "Gem Tools: a fast and efficient approach to estimating genetic ancestry," (Feb. 2011).

Laemmli U.K., "Cleavage of Structural Proteins during the Assembly of the Head of Bacteriophage T4," Nature 227:680-685 (1970).

LaRusch et al., "Whole Exome Sequencing Identifies Multiple, Complex Etiologies in an Idiopathic Hereditary Pancreatitis Kindred," JOP. J Pancreas (Online) 13(3):258-262 (2012).

Lasson et al., "Elevated Pancreatic Secretory Trypsin Inhibitor Levels during Severe Inflammatory Disease, Renal Insufficiency, and after Various Surgical Procedures," Scand J Gastroenterol 21:1275-1280 (1986).

Laurila et al., "Tight Junction Proteins in Gallbladder Epithelium: Different Expression in Acute Acalculous and Calculous Cholecystitis," The Journal of Histochemistry and Cytochemistry 55(6):567-573 (2007).

Lee et al., "Immunohistochemical analysis of claudin expression in pancreatic cystic tumors," Oncology Reports 25:971-978 (2011).

Liggins et al., "MORC4, a novel member of the MORC family, is highly expressed in a subset of diffuse large B-cell lymphomas," British Journal of Haematology 138:479-486 (2007).

Mankertz et al., "Functional crosstalk between Wnt signaling and Cdx-related transcriptional activation in the regulation of the claudin-2 promoter activity," Biochemical and Biophysical Research Communications 314:1001-1007 (2004).

Mankertz et al., "TNFα up-regulates claudin-2 expression in epithelial HT-29/B6 cells via phosphatidylinositol-3-kinase signaling," Cell Tissue Res 336:67-77 (2009).

Marks et al., "Chronic Pancreatitis in the Western Cape," Digestion 9:447-453 (1973).

Masson et al. "Trypsinogen Copy Number Mutations in Patients With Idiopathic Chronic Pancreatitis," Clin Gastroenterol and Hepatol 6:82-88 (2008).

Meriläinen et al., "Acute edematous and necrotic pancreatitis in a porcine model," Scandinavian Journal of Gastroenterology 43(10):1259-1268 (2008).

Naj et al., "Common variants at MS4A4/MS4A6E, CD2AP, CD33 and EPHA1 are associated with late-onset Alzheimer's disease," Nature Genetics 43(5):436-441 (2011).

Ogawa, M., "Pancreatic Secretory Trypsin Inhibitor as an Acute Phase Reactant," Clin Biochem 21:19-25 (1988).

Pfützer et al., "SPINK1/PSTI Polymorphisms Act as Disease Modifiers in Familial and Idiopathic Chronic Pancreatitis," Gastroenterology 119:615-623 (2000).

Price et al., "Principal components analysis corrects for stratification in genome-wide association studies," Nature Genetics 38(8):904-909 (2006).

Purcell et al., "PLINK: A Tool Set for Whole-Genome Association and Population-Based Linkage Analyses," American Journal of Human Genetics 81:559-575 (2007).

Racz et al., "Extracellular calcium sensing receptor in human pancreatic cells," Gut 51:705-711 (2002).

Robles-Diaz et al., "Chronic Pancreatitis in Mexico City," Pancreas 5(4):479-483 (1990).

Rosendahl et al., "Chymotrypsin C (CTRC) variants that diminish activity or secretion are associated with chronic pancreatitis," Nat Genet 40:78-82 (2008).

Rosendahl et al., "Risk contribution of SNPs rs10273639, rs7057398, and rs12688220 to alcoholic chronic pancreatitis," Pancreatology, 13(3):S9, 0-20 Abstract id:322 (May 2013).

Sakaguchi et al., "Cloning of the Human Claudin-2 5'-Flanking Region Revealed a TATA-less Promoter with Conserved Binding Sites in Mouse and Human for Caudal-related Homeodomain Proteins and Hepatocyte Nuclear Factor-1α*," The Journal of Biological Chemistry 277(24):21361-21370 (2002).

Schmid-Kotsas et al., "Lipopolysaccharide-Activated Macrophages Stimulate the Synthesis of Collagen Type I and C-Fibronectin in Cultured Pancreatic Stellate Cells," The American Journal of Pathology 155(5):1749-1758 (1999).

Schneider et al., "Combined Bicarbonate Conductance-Impairing Variants in CFTR and SPINK1 Variants are Associated With Chronic Pancreatitis in Patients Without Cystic Fibrosis," Gastroenterology 140:162-171 (2011).

Skol et al., "Joint analysis is more efficient than replication-based analysis for two-stage genome-wide association studies," Nature Genetics 38(3):209-213 (2006).

Suzuki et al., "Interleukin-6 (IL-6) Regulates Claudin-2 Expression and Tight Junction Permeability in Intestinal Epithelium," The Journal of Biological Chemistry 286(36):31263-31271 (2011).

Szmola et al., "Chymotrypsin C (caldecrin) promotes degradation of human cationic trypsin: Identity with Rinderknecht's enzyme Y," PNAS 104(27):11227-11232 (2007).

Teich et al., "Mutations of Human Cationic Trypsinogen (PRSS1) and Chronic Pancreatitis," Human Mutation 27(8):721-730 (2009).

The 1000 Genomes Project Consortium, "A map of human genome variation from population-scale sequencing," Nature 467:1061-1073 (2010).

Towbin et al., "Electrophoretic transfer of proteins from polyacrylamide gels to nitrocellulose sheets: Procedure and some applications," Proc. Natl. Acad. Sci. USA 76(9):4350-4354 (1979).

Van den Bossche, J. et al., "Claudin-1, Claudin-2 and Claudin-11 Genes Differentially Associate with Distinct Types of Anti-inflammatory Macrophages in vitro and with Parasite- and Tumour-elicited Macrophages In vivo," Scandinavian Journal of Immunology 75:588-98 (2012).

Van Itallie et al., "The density of small tight junction pores varies among cell types and is increased by expression of claudin-2," Journal of Cell Science 121:298-305 (2008).

Whitcomb et al. "Hereditary pancreatitis is caused by a mutation in the cationic trypsinogen gene," Nature Genetics 14:141-145 (1996).

Whitcomb et al., "Common genetic variants in the CLDN2 and PRSS1-PRSS2 loci alter risk for alcohol-related and sporadic pancreatitis," Nat Genet., 44(12):1349-1354 (2012).

Whitcomb et al., "Multicenter Approach to Recurrent Acute and Chronic Pancreatitis in the United States: The North American Pancreatitis Study 2 (NAPS2)," Pancreatology 8:520-531 (2008).

Whitcomb, "What is personalized medicine and what should it replace?" Nat. Rev. Gastroenterol. Hepatol. 9(7):418-424 (2012).

Whitcomb et al., "Angiopoietin-2, a Regulator of Vascular Permeability in Inflammation, Is Associated With Persistent Organ Failure in Patients With Acute Pancreatitis From the United States and Germany," Am J Gastroenterol 105:2287-2292 (2010).

Witt et al. "A degradation-sensitive anionic trypsinogen (PRSS2) variant protects against chronic pancreatitis," Nat Genet 38(6):668-673 (2006).

Witt et al., "Chronic Pancreatitis: Challenges and Advances in Pathogenesis, Genetics, Diagnosis, and Therapy," Gastroenterology 132:1557-1573 (2007).

(56) References Cited

PUBLICATIONS

Yadav et al., "Alcohol Consumption, Cigarette Smoking, and the Risk of Recurrent Acute and Chronic Pancreatitis," Arch Intern Med. 169(11):1035-1045 (2009).

Yadav et al., "Pancreatitis: Prevalence and Risk Factors Among Male Veterans in a Detoxification Program," Pancreas 34:390-398 (2007).

Yadav et al., "The role of alcohol and smoking in pancreatitis," Nat. Rev. Gastroenterol. Hepatol. 7:131-145 (2010).

Yang et al., "GCTA: A Tool for Genome-wide Complex Trait Analysis," The American Journal of Human Genetics 88:76-82 (2011).

Zheng et al., "Testing Association for Markers on the X Chromosome," Genetic Epidemiology 31:834-843 (2007).

\* cited by examiner

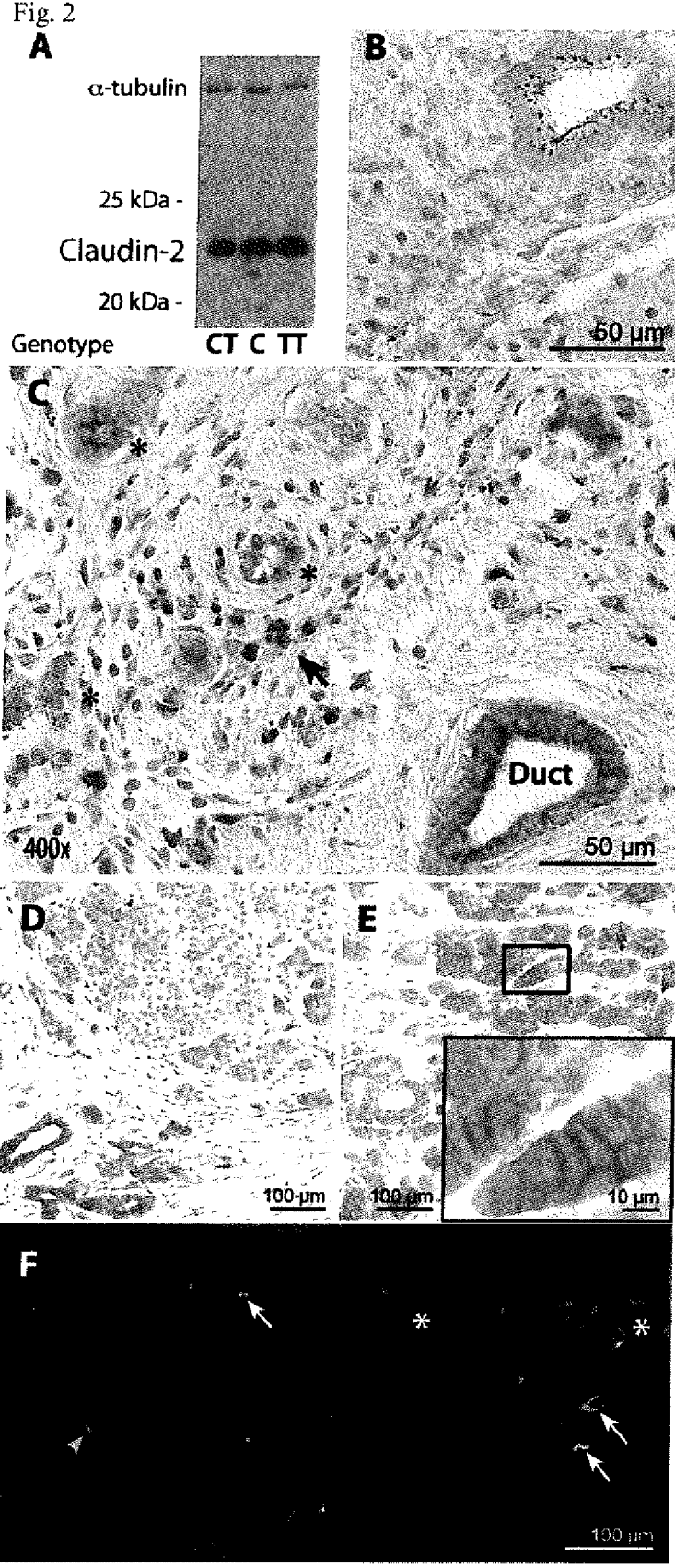

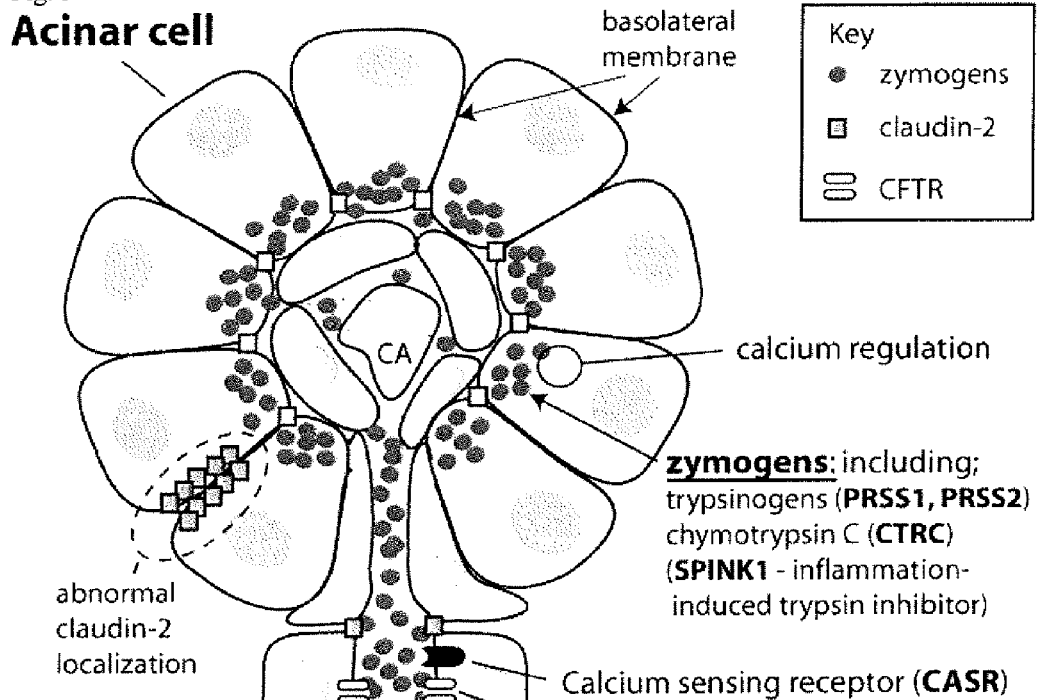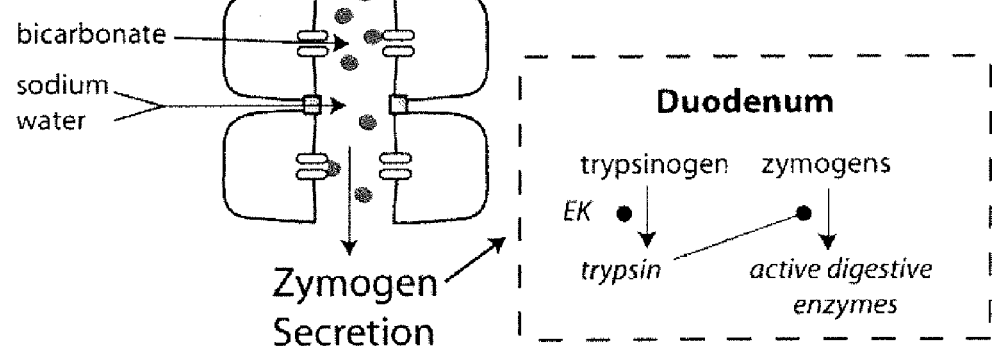

FIG. 12

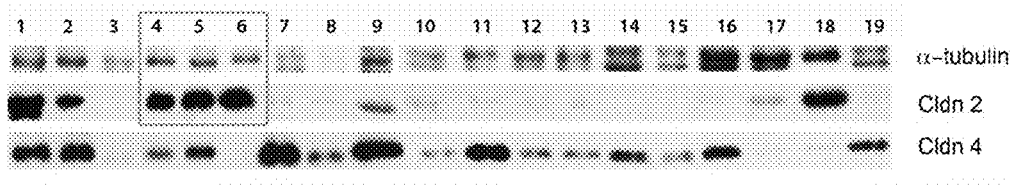

| Sample | Histology | Cldn-2 | Cldn-4 |
|---|---|---|---|
| Low risk (C/CC) | | | |
| 1 female | 33% acini/duct, 33% islets, 33% fat<br>no inflammation | ++++ | +++ |
| 2 male | 40% atrophic acini/duct, 33% fibrosis, 25% fat, 2% islets<br>no inflammation | ++ | ++++ |
| 5 male | 25% acini/duct, 5% islets; 70% fibrosis<br>focal chronic inflammation | ++++ | ++ |
| 8 male | 90% acini/duct, 5% islets, 5% fibrosis<br>no inflammation | - | ++ |
| 11 female | 95% acini/duct, 2% islets, 3% fat & fibrosis<br>no inflammation | - | +++ |
| 17 male | 85% acini/duct, 5% islets, 5% fat, 5% fibrosis,<br>no inflammation | + | - |
| 18 female | 65% partially atrophic acini/duct, 5% fibrosis,<br>30% fat & fibrosis<br>mild to moderate chronic inflammation | ++++ | + |
| 19 male | all acini/duct, trace islets fat & fibrosis;<br>no inflammation | - | ++ |
| Low risk (CT) | | | |
| 4 female | 5% atrophic acini/duct, 45% fibrosis, 50% fat<br>mild chronic inflammation | +++ | + |
| 7 female | 90% acini/duct, 5% islets, 5% fibrosis<br>no inflammation | - | ++++ |
| 9 female | 70% acini/duct 5% islets, 5% fibrosis 20% fibroadipose tissue<br>no inflammation | + | ++++ |
| 10 female | All cancer | + | + |
| 12 female | 67% acini/duct, 33% fat<br>no inflammation | - | ++ |

FIG. 12 (Cont.)

| 13 | female | 60% acini/duct, 40% fibrosis<br>mild Chronic inflammation | - | ++ |
|---|---|---|---|---|
| 15 | female | all acini/duct, rare fat, fibrosis and islets<br>no inflammation | - | + |
| High risk (T, TT) | | | | |
| 3 | male | 75% acini/duct, 20% fibrosis, 5% islets;<br>no inflammation | - | - |
| 6 | female | 80% atrophic acini/duct, 15% fibrosis,<br>5% islets<br>mild chronic inflammation | ++++ | - |
| 14 | male | 85% acini/duct, 5% fibrosis and islets,<br>10% fat<br>no inflammation | - | ++ |
| 16 | male | 90% acini/duct, 5% fat, 5% fibrosis and islets<br>no Inflammation | - | +++ |

METHOD FOR DIAGNOSING AND ASSESSING RISK OF PANCREATITIS USING GENETIC VARIANTS

PRIORITY CLAIM

This application is a continuation of International Patent Application Serial No. PCT/US13/069676, filed Nov. 12, 2013 and claims priority to U.S. Provisional Application Ser. No. 61/724,568, filed Nov. 9, 2012, the contents of both of which are incorporated by reference in their entireties herein.

GRANT INFORMATION

This invention was made with government support under Grant No. DK061451, awarded by the National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Jul. 21, 2015, is named 072396.0596_SL.txt and is 1,213 bytes in size.

BACKGROUND

Chronic inflammation is a variable and unpredictable complication of tissue injury or stress in humans. Chronic inflammation of the pancreas leads to irreversible destruction, known as chronic pancreatitis. Pancreatitis is a complex, progressively destructive inflammatory disorder. Inflammatory changes of the pancreas involving some or all of the following: fibrosis, calcification, pancreatic ductal inflammation, and pancreatic stone formation. Alcohol was long thought to be the primary causative agent, but genetic contributions have been of interest since the discovery that rare PRSS1, CFTR, and SPINK1 variants were associated with pancreatitis risk.

SUMMARY OF THE APPLICATION

The present application provides for methods for predicting the risk of developing, or the presence of, recurrent acute pancreatitis and/or chronic pancreatitis, in a subject, by identifying the presence of an rs12688220 T allele, an rs7057398 T allele, and/or an rs10273639 C allele in a sample from the subject.

In certain embodiments, the methods for predicting the risk of developing, or the presence of, recurrent acute pancreatitis and/or chronic pancreatitis, in the subject comprise testing a sample from the subject for the presence of the rs12688220 T allele, the rs7057398 T allele, and/or the rs10273639 C allele, wherein the testing step comprises a nucleic acid detection assay selected from the group consisting of polymerase chain reaction, quantitative polymerase chain reaction, nucleic acid sequencing, and nucleic acid microarray analysis.

In certain embodiments, the methods of the present application further comprise administering one or more treatments for pancreatitis to the subject when the rs12688220 T allele, the rs7057398 T allele, and/or the rs10273639 C allele is detected in the sample from the subject.

In certain embodiments, the application provides for methods of treating or preventing pancreatitis in a subject in need thereof comprising testing a sample from the subject for the presence of the rs12688220 T allele, the rs7057398 T allele, and/or the rs10273639 C allele, wherein the testing step comprises a nucleic acid detection assay selected from the group consisting of polymerase chain reaction, quantitative polymerase chain reaction, nucleic acid sequencing, and nucleic acid microarray analysis, and administering a treatment for pancreatitis to the subject if the rs12688220 T allele, the rs7057398 T allele, and/or the rs10273639 C allele is detected in the sample.

DESCRIPTION OF THE FIGURES

FIG. 2. Expression and localization of claudin-2 in the human pancreas using mouse anti-claudin-2 antibodies based on rs12688220 genotype. A. Western blot of anti-claudin-2 antibody from 3 control samples genotyped at rs12688220 (TT is high risk). The antibody reacts with a protein at ~22-23 kDa, consistent with claudin-2. Samples had inflammation and/or fibrosis on histology of adjacent tissue. α-tubulin, loading control. Blots from all controls are presented in FIG. 10. B. Anti-claudin-2 staining (brown color) of normal-appearing control tissue localizing to ducts but not to acinar cells (scale bar=50 μm). C. Severe chronic pancreatitis from a case with the high-risk (T male or TT female) genotype. Claudin-2 staining localizes to the intralobular duct (Duct), atrophic acini (*), and cells with morphologic appearance of macrophages (arrow)(scale bar=50 μm). D. Chronic pancreatitis tissue from a patient with the low-risk genotype (CC or CT) with staining localizing to the duct and granular staining in acinar cells (scale bar=100 μm). E. Chronic pancreatitis, high-risk genotype with intense staining of acinar cell basolateral membrane (scale bar=100 μm, enlarged in inset, scale bar=10 m). F. Immunofluorescence staining of control human pancreatic tissue claudin-2 staining (red) localizing to the ducts (*) and co-localizing with the macrophage marker CD68 (green, colocalized with red is yellow, arrows. Nuclei stained with Hoechst's dye, blue, scale bar=100 μm).

FIG. 3. Model of a pancreatic acinus illustrating pancreatic zymogen secretion from the acinar cells into the ducts, the relationship between acinar and duct cells, and the secretory pathway of the zymogens (digestive pro-enzymes), including trypsinogen to the duodenum, where they are activated. At least five genes have been identified as risk factors for chronic pancreatitis (CP) and replicated in multiple populations[2,3]. Gain-of-function mutations in the cationic trypsinogen gene (PRSS1) (e.g., p.N29I, p.R122H) cause hereditary pancreatitis[8], an autosomal dominant form of CP that begins with RAP and progresses to CP. Cationic and anionic trypsin are the master enzymes of the pancreas in that they regulate activation of the other pancreatic digestive zymogens following their own activation by enterokinase (EK) in the duodenum. Premature trypsin activation in the acinar cell or duct leads to zymogen activation, injury, and pancreatitis. Failure to inactivate trypsin directly (SPINK1 mutations, CTRC mutations); to control calcium concentrations in the acinar cell (calcium regulation) or duct (CASR mutations) and thus enhance trypsin activation and survival; or to flush trypsin out of the pancreatic ducts (CFTR mutations) all increase the risk of developing pancreatitis. CA=centroacinar cells, a type of duct cell. Claudin-2 is normally expressed between duct cells, but abnormal localization may occur in association with a CLDN2 risk allele (described in the text) during pancreatic inflammation. For further discussion, see Example 1, "Protein-protein and system-based interactions among genes with variants associated with recurrent acute and chronic pancreatitis."

FIG. 12. Control pancreatic tissue Western blot. Effect of histology and rs12688220 genotype on claudin-2 expression. Top panel. Western blot of 19 control samples for claudin-2, α-tubulin (loading control), and claudin-4 (comparison molecule). Blue box outlines the samples used in the text (FIG. 3A). Claudin-2 is up-regulated and claudin-4 down-regulated by inflammation in gallbladder[10]; this general pattern is confirmed in the pancreas. Claudin-2 is also expressed in islets, which were abundant in sample 1. Bottom panel. Details of the histological evaluation of the tissue adjacent to the sample used in the Western blot, organized by rs12688220 genotype. Cldn-2 and Cldn-4 are qualitative indicators of the density of staining in the top panel, to assist in review. The pattern is consistent with claudin-2 immunohistochemistry, which demonstrates strong up-regulation during inflammation (FIG. 2 B non-inflamed versus C-E inflamed).

DETAILED DESCRIPTION

Figure 1:
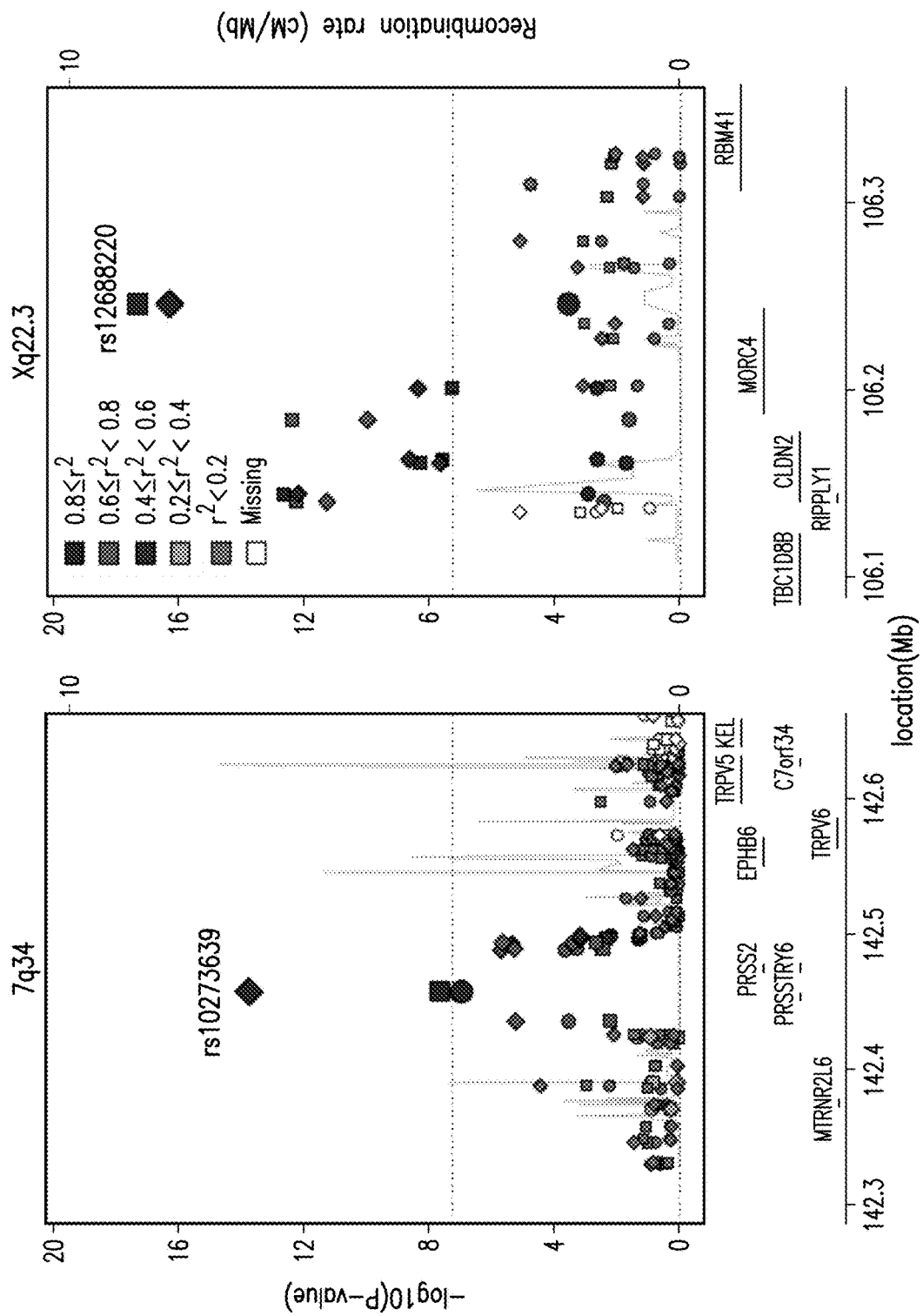
FIG. 1. Manhattan plot showing the negative log (base 10) of the p-value for the association of SNP genotype with affection status for all SNPs passing quality control filters and falling within a selected region of the PRSS1-PRSS2 and CLDN2 loci. Regions selected to highlight the most associated SNPs. Squares indicate Stage 1 results, circles for Stage 2, diamonds for combined Stage 1 and 2 data. After accounting for the most highly associated SNP at each locus, no other SNP approached genomewide-significant association.

The present disclosure is based, at least in part, on the discovery of alleles within the CLDN2 locus and the PRSS1-PRSS2 locus that are associated with recurrent acute pancreatitis and/or chronic pancreatitis.

In particular, subjects with a particular genetic signature on chromosome X, identified as the CLDN2 locus, have a higher risk of developing chronic pancreatitis than subjects who do not have this high-risk locus. These high risk alleles in the CLDN2 locus are defined by the rs12688220 T allele and the rs7057398 T allele, and polymorphisms in linkage disequilibrium with these alleles.

In certain embodiments, the rs12688220 C allele is a human allele, and comprises the human nucleic acid sequence TTTACCCCCAT (SEQ ID NO: 1), wherein the rs12688220 C allele SNP is in bold and underlined text. In alternative embodiments, an alternative allele at this position, rather than C, is T, as in SEQ ID NO:2.

In certain embodiments, the rs12688220 T allele is a human allele, and comprises the human nucleic acid sequence TTTACTCCCAT (SEQ ID NO:2), wherein the rs12688220 T allele SNP is in bold and underlined text. In alternative embodiments, an alternative allele at this position, rather than T, is C, as in SEQ ID NO: 1.

In certain embodiments, the rs7057398 T allele is a human allele, and comprises the human nucleic acid sequence GCCTCTAGAAA (SEQ ID NO:3), wherein the rs7057398 T allele SNP is in bold and underlined text. In alternative embodiments, an alternative allele at this position, rather than T, is C, as in SEQ ID NO:4.

In certain embodiments, the rs7057398 C allele is a human allele, and comprises the human nucleic acid sequence GCCTCCAGAAA (SEQ ID NO:4), wherein the rs7057398 C allele SNP is in bold and underlined text. In alternative embodiments, an alternative allele at this position, rather than C, is T, as in SEQ ID NO:3.

Similarly, subjects with a particular genetic signature on chromosome 7, identified as the PRSS1-PRSS2 locus, have a higher risk of developing recurrent acute pancreatitis and chronic pancreatitis than subjects who do not have this high-risk locus. This high risk allele in the PRSS1-PRSS2 locus is defined by the rs10273639 C allele, and polymorphisms in linkage disequilibrium with this allele. Conversely, the presence of the minor T allele at this locus confers lower risk.

In certain embodiments, the rs10273639 C allele is a human allele, and comprises the human nucleic acid sequence ACCAACGCTTG (SEQ ID NO:5), wherein the rs10273639 C allele SNP is in bold and underlined text. In alternative embodiments, an alternative allele at this position, rather than C, is T, as in SEQ ID NO:6.

In certain embodiments, the rs10273639 T allele is a human allele, and comprises the human nucleic acid sequence ACCAATGCTTG (SEQ ID NO:6), wherein the rs10273639 T allele SNP is in bold and underlined text. In alternative embodiments, an alternative allele at this position, rather than T, is C, as in SEQ ID NO:5.

The risk for chronic pancreatitis is further increased in subjects who drink alcohol, such that nearly half of all subjects tested that have so-called alcoholic pancreatitis also have both rs10273639 (PRSS1-PRSS2 locus) and rs12688220 (CLDN2 locus) (see Table 3). This is the first genetic variable to predict risk of progressive inflammation in the pancreas, with higher risk in patients who drink alcohol.

With respect to the CLDN2 locus, as it is an X chromosome marker, it has different risk in men than women, as seen in chronic pancreatitis, sclerosing cholangitis, and ulcerative colitis.

As described herein, subjects with the high risk CLDN2 locus have aberrant localization of the claudin-2 protein. This protein is found in areas of destructive inflammation. Furthermore, claudin-2 is present in human biliary duct, small intestine, macrophages and neurons, suggesting that these cells and tissues are at increased risk for abnormal CLDN2 regulation and chronic inflammation. Therefore, localization of claudin-2 can be predictive of chronic inflammation, e.g., chronic pancreatitis.

As also described herein, rs10273639, which is present in the 5' promoter region of PRSS1 (encoding for trypsinogen), affects expression of PRSS1. In particular, expression levels of PRSS1 were highest in homozygous subjects with two C alleles at rs10273639, intermediate in heterozygotes, and lowest in subjects with two T alleles at rs10273639. Therefore, without being bound by theory, rs10273639 C appears to increase expression of the trypsinogen enzyme which increases risk for recurrent acute pancreatitis and chronic pancreatitis.

The present disclosure provides methods for predicting the risk of developing, or the presence of, recurrent acute pancreatitis and/or chronic pancreatitis, in a subject, by identifying the presence of one or more of the polymorphisms identified herein, or polymorphisms in linkage disequilibrium with these alleles (e.g., surrogate markers), in a sample obtained from the subject.

In certain embodiments, the present disclosure provides for methods for predicting the risk of developing, or the presence of, recurrent acute pancreatitis and/or chronic pancreatitis, in a subject, by identifying the presence of the rs12688220 T allele, the rs7057398 T allele, and/or the rs10273639 C allele, wherein the method comprises testing a sample from the subject for the presence of the rs12688220 T allele, the rs7057398 T allele, and/or the rs10273639 C allele, wherein the testing step comprises a nucleic acid detection assay selected from the group consisting of polymerase chain reaction, quantitative polymerase chain reaction, nucleic acid sequencing, and nucleic acid microarray analysis.

In one embodiment, the presence of one or both of the rs7057398 T allele or the rs12688220 T allele, or polymorphisms in linkage disequilibrium with one or both of alleles, in a sample obtained from a subject, indicates that the subject is at increased risk (relative to a subject lacking said genotype) for developing, or is suffering from, chronic pancreatitis.

In another embodiment, the presence of the rs10273639 C allele, or polymorphisms in linkage disequilibrium with this allele, in a sample obtained from a subject, indicates that the subject is at increased risk (relative to a subject lacking said genotype) for developing, or is suffering from, recurrent acute pancreatitis or chronic pancreatitis.

The subject may be a human or non-human subject. Examples of non-human subjects include dog, cat, rodent, cow, sheep, pig, or horse, to name a few.

It may be particularly desirable to assess the genotype as described herein in human subjects with a history of alcohol abuse and/or pancreatitis.

If a diagnosis of pancreatitis is indicated based on the methods disclosed herein, a healthcare provider can optionally take the further step of recommending and/or performing a further diagnostic test for pancreatitis. In one embodiment, exemplary diagnostic tests for pancreatitis include biochemical measurements, such as measurements for abnormal levels of isoamylase, lipase, trypsin, elastase, or secretin, quantitative measurement of fecal fat, measurement of plasma cholecystokinin (CCK), tests for pancreatic exocrine function, radiological testing such as plain abdominal film, transabdominal ultrasound, or CT scanning, magnetic resonance cholangiopancreatography (MRCP), or endoscopic diagnosis, e.g., endoscopic retrograde cholangiopancreatography (ERCP) or endoscopic ultrasonography.

The present disclosure also provides methods for predicting the risk of developing, or the presence of, recurrent acute pancreatitis and/or chronic pancreatitis, in a sample obtained from a subject, by identifying increased expression or activity of PRSS1, wherein increased expression or activity of PRSS1 indicates that the subject is at risk for developing, or is suffering from, recurrent acute pancreatitis and/or chronic pancreatitis.

In another aspect, the disclosure provides methods for predicting the risk of developing, or the presence of, chronic pancreatitis, by detecting aberrant localization of the claudin-2 protein in a subject, wherein aberrant localization indicates that the subject is at risk for developing, or is suffering from, chronic pancreatitis.

The present disclosure also provides methods for treating or preventing pancreatitis by identifying a subject that is at risk for developing, or is suffering from, recurrent acute pancreatitis and/or chronic pancreatitis, based on the methods described herein, and subsequently treating the subject for pancreatitis, e.g., recurrent acute pancreatitis and/or chronic pancreatitis. Treatment includes treating recurrent acute pancreatitis and/or chronic pancreatitis or symptoms thereof, or preventing recurrence or progression of recurrent acute pancreatitis and/or chronic pancreatitis.

In one embodiment, treatment for acute pancreatitis or chronic pancreatitis includes, for example, pain management, abstinence from alcohol and cigarette smoking, cholecystectomy, biliary sphincterotomy, endoscopic retrograde cholangiopancreatography (ERCP), administration of intravenous fluids, nutritional support, antibiotics, carbapenems, enzyme therapy, surgery, such as longitudinal pancreaticojejunostomy or pancreatoduodenectomy, distal pancreatectomy, celiac nerve block, endoscopic therapy, and/or percutaneous drainage. Other known methods for treatment or prevention of pancreatitis within the knowledge of the healthcare provider, are included herein.

In certain embodiments, the application provides for methods of treating or preventing pancreatitis in a subject in need thereof comprising testing a sample from the subject for the presence of the rs12688220 T allele, the rs7057398 T allele, and/or the rs10273639 C allele, wherein the testing step comprises a nucleic acid detection assay selected from the group consisting of polymerase chain reaction, quantitative polymerase chain reaction, nucleic acid sequencing, and nucleic acid microarray analysis, and administering a treatment for pancreatitis to the subject if the rs12688220 T allele, the rs7057398 T allele, and/or the rs10273639 C allele is detected in the sample.

The present disclosure provides various methods of testing for one or more polymorphism in the CLDN2 locus and/or the PRSS1-PRSS2 locus, and polymorphisms in linkage disequilibrium therewith. Numerous procedures for determining the nucleotide sequence of a nucleic acid, or for determining the presence of mutations in nucleic acids include a nucleic acid amplification step, which can be carried out by, e.g., polymerase chain reaction (PCR). In other non-limiting embodiments, any method known may be used for determining the nucleic acid sequence, such as, for example, quantitative PCR, nucleic acid sequencing, and nucleic acid microarray analysis. Accordingly, in one embodiment, the invention provides primers for amplifying a portion of an CLDN2 locus and/or a PRSS1-PRSS2 locus comprising a polymorphic region of which specific allelic variants are associated with pancreatitis. In a preferred embodiment, the portion of the CLDN2 locus and/or PRSS1-PRSS2 locus will be amplified to, e.g., detect which allelic variant of a polymorphic region is present in the CLDN2 locus and/or PRSS1-PRSS2 locus of a subject. Probes can also be used in diagnostic assays, wherein, for example, a probe comprises a region having a nucleotide sequence that hybridizes to an CLDN2 locus and/or a PRSS1-PRSS2 locus comprising a polymorphic region of which specific allelic variants are associated with pancreatitis.

The polymorphisms of the present disclosure can also be identified using, for example, nucleic acid sequencing or microarray analysis (to identify more than one polymorphism in a sample). Any method known in the art for testing for polymorphisms can be used in the methods of the invention.

In certain embodiments, the present disclosure provides for a kit for detecting at least one or more polymorphism in the CLDN2 locus and/or the PRSS1-PRSS2 locus, e.g., the rs12688220 T allele, the rs7057398 T allele, and/or the rs10273639 C allele, and polymorphisms in linkage disequilibrium therewith, wherein the kit comprises one or more oligonucleotide probe or primers, each of which is capable of specifically hybridizing to genomic DNA associated with a CLDN2 locus and/or PRSS1-PRSS2 locus as described herein.

Example 1

We now report two significant genome-wide associations identified and replicated at PRSS1-PRSS2 ($1\times10^{-12}$) and x-linked CLDN2 ($p<1\times10^{-21}$) through a two-stage genome-wide study (Stage 1, 676 cases and 4507 controls; Stage 2, 910 cases and 4170 controls). The PRSS1 variant affects susceptibility by altering expression of the primary trypsinogen gene. The CLDN2 risk allele is associated with atypical localization of claudin-2 in pancreatic acinar cells. The homozygous (or hemizygous male) CLDN2 genotype confers the greatest risk, and its alleles interact with alcohol consumption to amplify risk. These results could partially explain the high frequency of alcohol-related pancreatitis in men-male hemizygous frequency is 0.26, female homozygote is 0.07.

The exocrine pancreas is a simple digestive gland of only two primary cell types, each with a single function (FIG. 3). Recurrent acute pancreatic inflammation can, but does not always, progress to irreversible damage of the gland, including fibrosis, atrophy, pain, and exocrine and endocrine insufficiency,[1-3] known as chronic pancreatitis. Different genetic and environmental factors produce the same clinical phenotype[4].

We collected biological samples and phenotypic data from 1000 patients with recurrent acute pancreatitis and chronic pancreatitis plus controls in the North American Pancreatitis Study 2 (NAPS2)[5]. The primary environmental risk factor identified was heavy alcohol drinking when symptoms of pancreatitis began, based on the assessment of the study physician, called herein alcohol-related pancreatitis.

Figure 6:
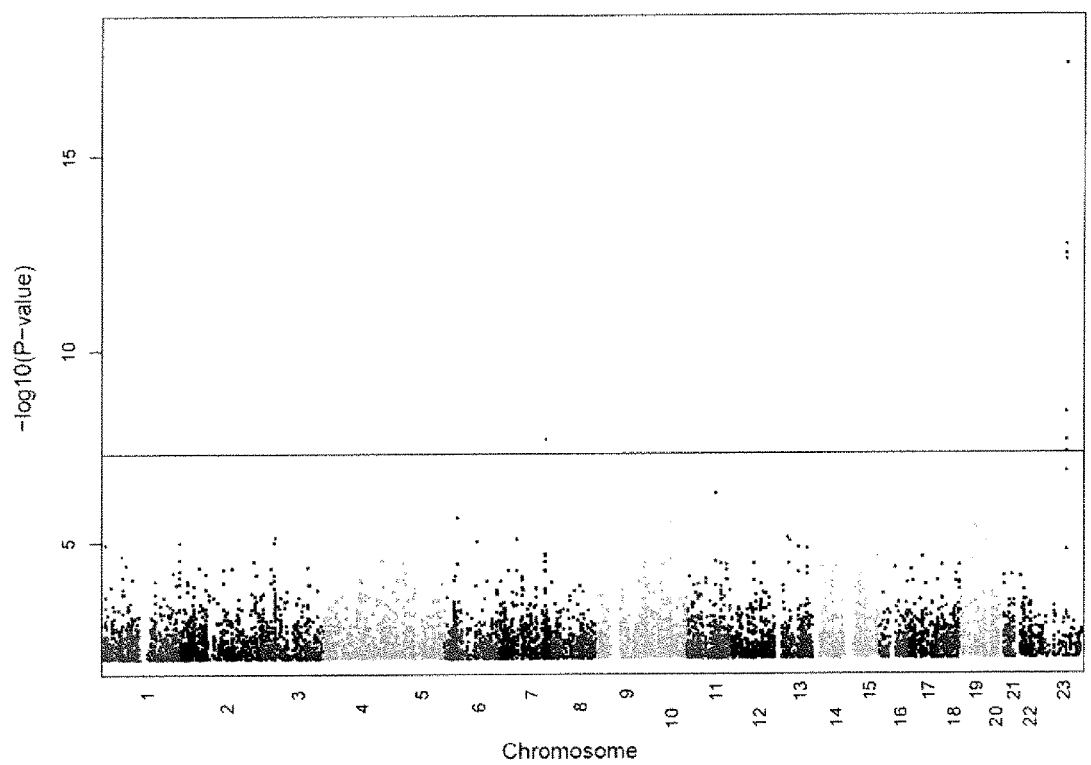
FIG. 6. Manhattan plot showing the negative log (base 10) of the p-value for association of SNP genotype with affection status (chronic pancreatitis versus control) for all SNPs passing quality control filters in Stage 1. Note the horizontal line at $5 \times 10^{-8}$, which denotes an accepted significance threshold for genome-wide association. SNPs in interval Xq23.3 (CLDN2 locus) cross this threshold, as does a SNPs in 7q34 (PRSS1-PRS S2 locus).
Figure 7:
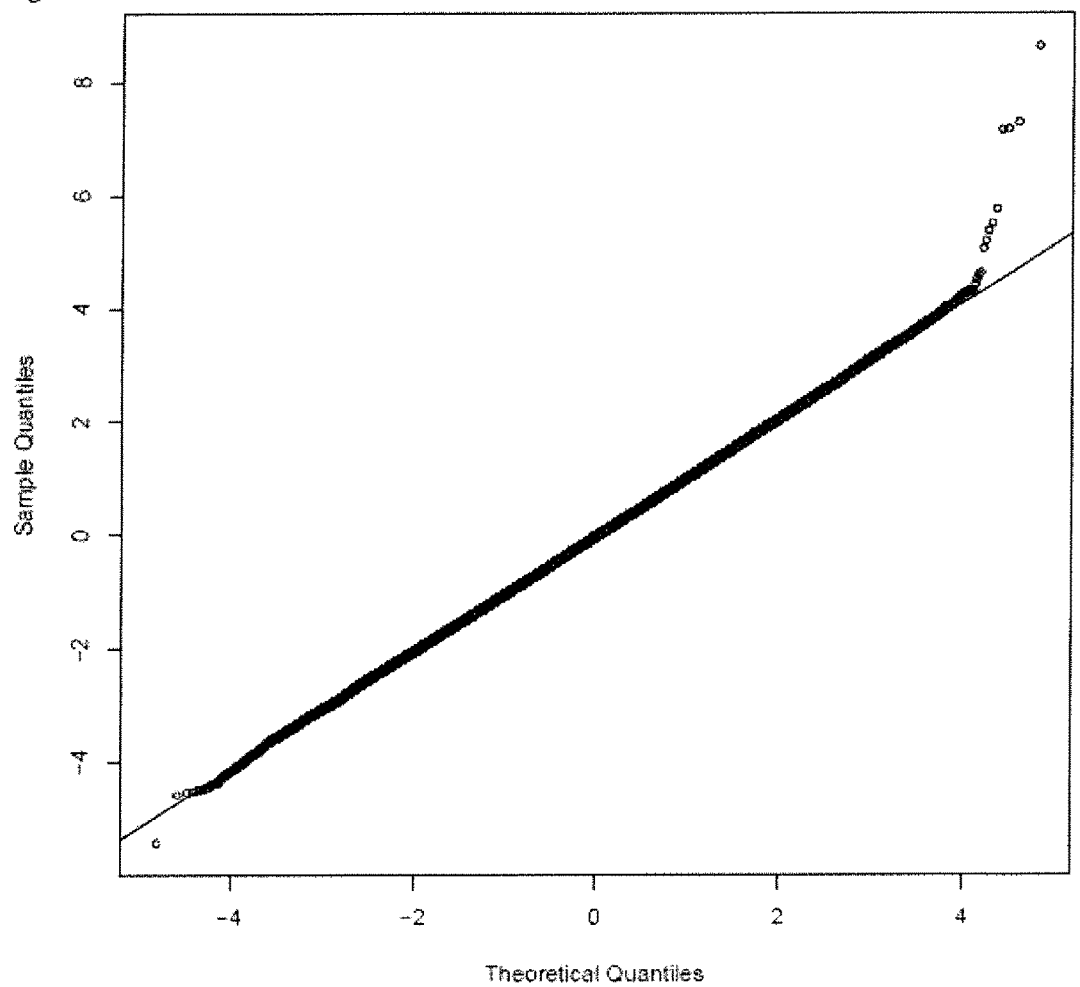
FIG. 7. Quantile-Quantile or Q-Q plot of association test statistics. Genomic inflation factor $\lambda=1.06$. If there were no difference between the observed distribution and that expected under the null hypothesis (no association), all points would fall on the line (X=Y).

To further define genetic risk, we conducted a two-stage (discovery/replication) genomewide association study (GWAS). The final data set for the Stage 1 cohort included 676 chronic pancreatitis cases and 4507 controls of European ancestry FIGS. 6-7) genotyped at 625,739 SNPs (Table 1; Table 4). Genomewide significant associations (p-value<$5\times10^{-8}$) were identified at two loci. The most highly associated SNP fell in Xq23.3, dubbed the CLDN2 locus, the other in 7q34, the PRSS1-PRSS2 locus (FIG. 1; Table 2; FIGS. 6-7, Table 5). CLDN2 encodes the protein claudin-2, while PRSS1 encodes cationic trypsinogen, and PRSS2 encodes anionic trypsinogen.

Figure 8:
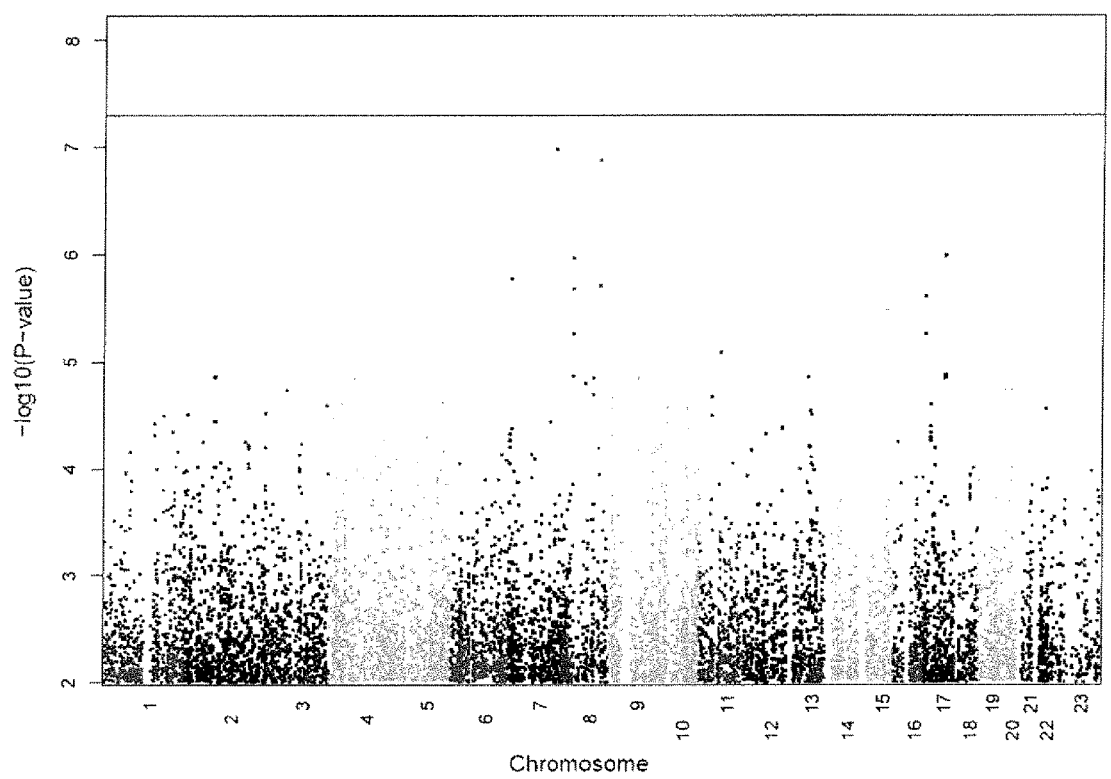
FIG. 8. Manhattan plot showing the negative log (base 10) of the p-value for association of SNP genotype with affection status (chronic pancreatitis and recurrent acute pancreatitis versus control) for all SNPs passing quality control filters in Stage 2. Note the horizontal line at $5 \times 10^{-8}$, which denotes an accepted significance threshold for genome-wide association. Genomic inflation factor $\lambda=1.09$.
Figure 9:
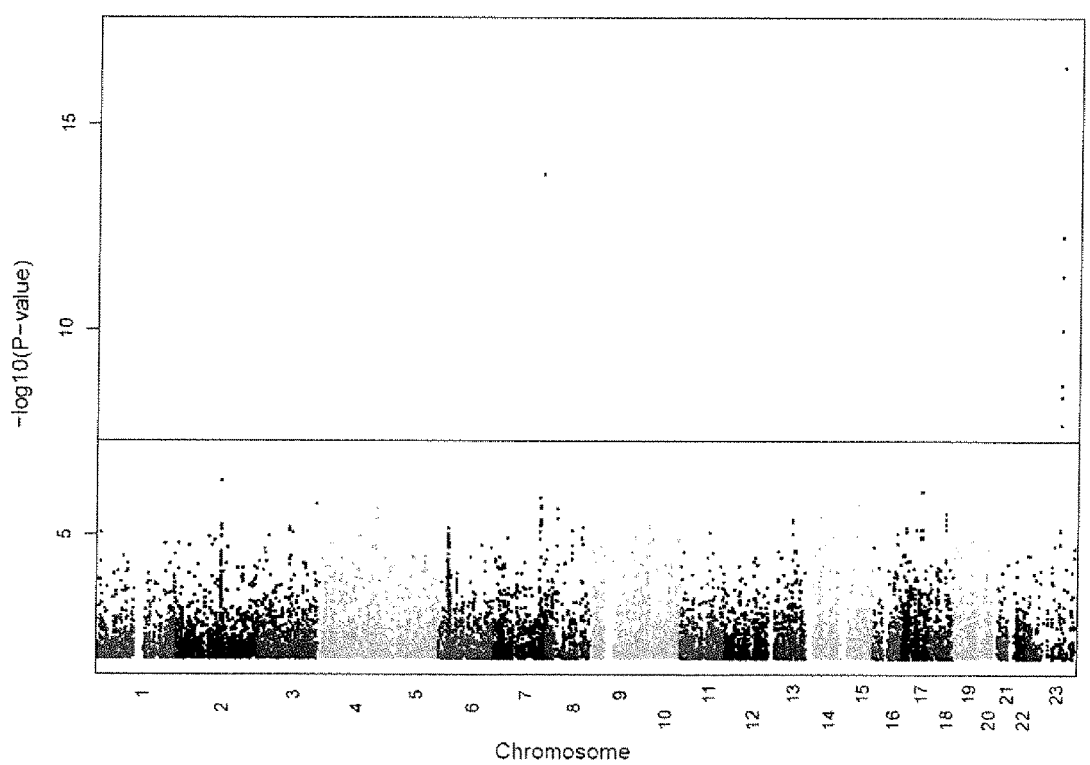
FIG. 9. Manhattan plot showing the negative log (base 10) of the p-value for association of SNP genotype with affection status (chronic pancreatitis and recurrent acute pancreatitis versus control) for all SNPs passing quality control filters in the combined data from Stages 1 and 2. Note the horizontal line at $5 \times 10^{-8}$, which denotes an accepted significance threshold for genome-wide association. SNPs in interval Xq23.3 (CLDN2 locus) cross this threshold, as does a SNP in 7q34 (PRSS1-PRSS2 locus). Genomic inflation factor $\lambda=1.13$.
Figure 10:
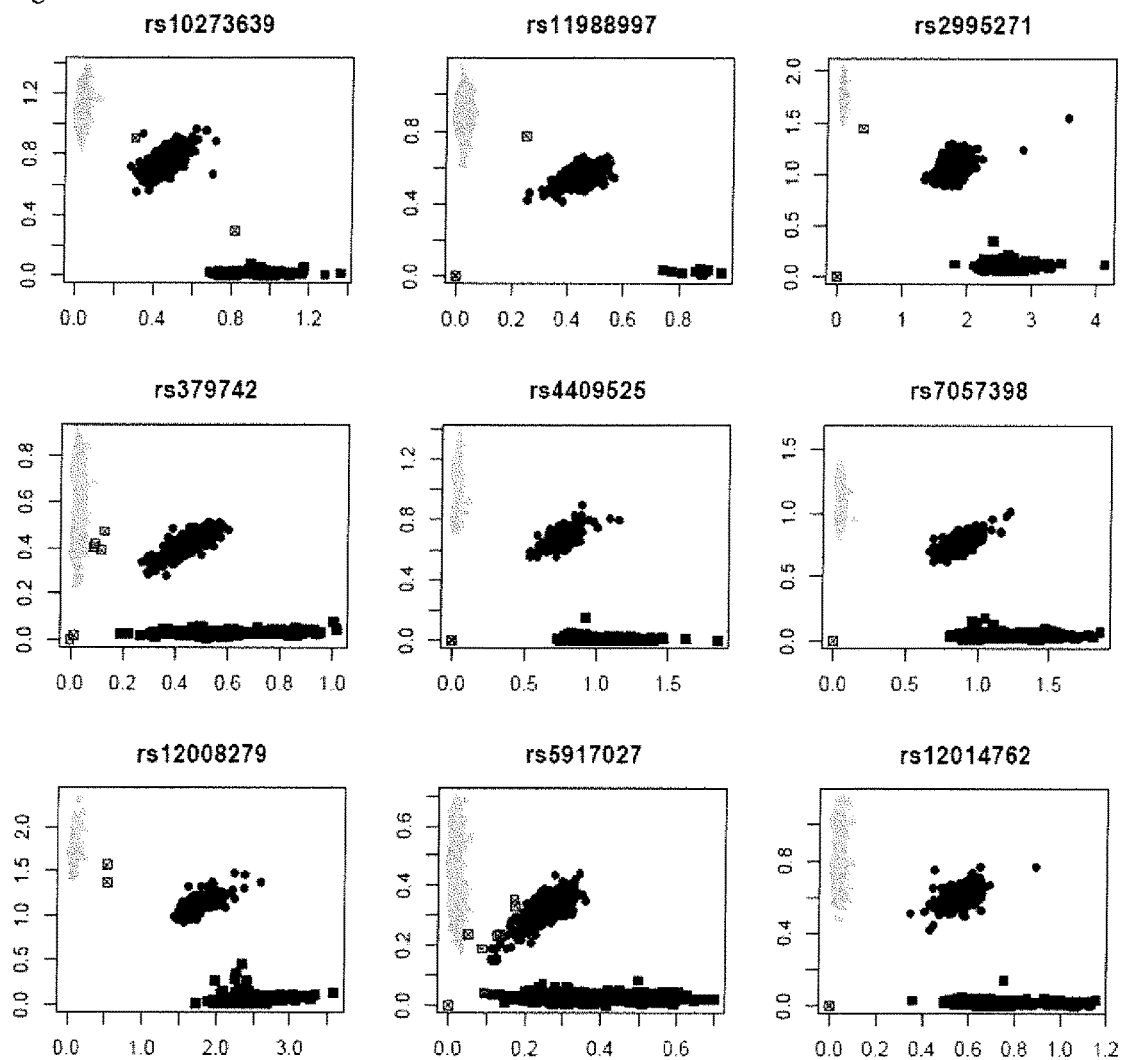
FIG. 10. SNP genotype clusters for SNPs having p-values<$5 \times 10^{-7}$ (as calculated by Plink) for the combined Stage 1 and 2 data. Green (triangles) and blue (squares) indicate called homozygotes, black (circles) called heterozygotes, and red (x in square) is non-called (missing) genotypes. Only SNPs having acceptable quality for genotype calls are shown. Note that rs10273639 (PRSS1-PRSS2 locus) and rs12688220 (CLDN2 locus) are the most highly associated SNPs for their respective loci.
Figure 10:
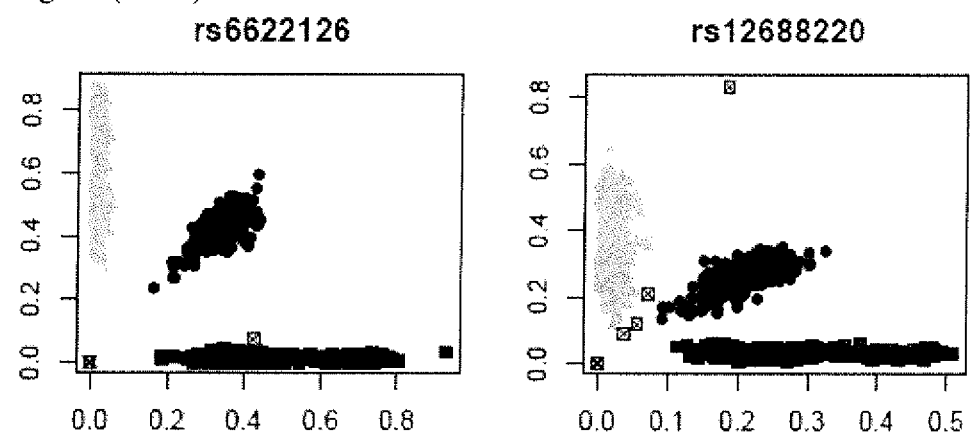

The Stage 2 cohort included 910 cases (331 chronic pancreatitis, 579 recurrent acute pancreatitis; Table 1, Table 4), again genotyped at 625,739 SNPs, and 4170 controls, most genotyped previously on the Illumina 1M. All subjects were of European ancestry as determined by genetic analyses. Recurrent acute pancreatitis and chronic pancreatitis were modeled as having common susceptibilities, with chronic pancreatitis occurring over time in the presence of additional disease-modifying factors.[6] It is possible that this assumption reduces power relative to a study comprising solely chronic pancreatitis or recurrent acute pancreatitis cases. Our primary targets in Stage 2 were the PRSS1-PRSS2 and CLDN2 loci, although we also conducted a joint analysis[7] of Stage 1 and Stage 2 data to uncover any new risk loci. After controlling for ancestry, these data demonstrated significant effects for the CLDN2 and PRSS1-PRSS2 loci (FIG. 1; Table 5-6; FIGS. 8-9). Quality of SNP genotypes supported the association (FIG. 10). The frequencies of the putative risk alleles at these 2 loci were 0.57 for the C allele at rs10273639 (PRSS1-PRSS2 locus), with the minor T allele reducing risk, and 0.26 for the T allele at rs12688220 (CLDN2 locus). No other locus shows association after accounting for SNP genotype quality (FIGS. 8-10).

PRSS1 gain-of-function mutations, such as p.R122H, increase risk for recurrent acute pancreatitis and chronic pancreatitis[8], as do increased copy number[9,10]. Rare loss-of-function mutations in PRSS2 are protective[11]. However, rs10273639 is in the 5' promoter region of PRSS1. Because it is the only highly associated SNP in the locus, we validated its genotypes by independent TaqMan genotyping and also genotyped two SNPs in linkage disequilibrium with it (footnote, Table 7)[12, 13]. We screened PRSS1 for rare variants in 1138 subjects: 418 chronic pancreatitis, 350 recurrent acute pancreatitis, and 379 controls. Three known disease-associated variants (A16V, N29I, R122H) were identified in 23 subjects (Table 7). These gain-of-function variants occur almost solely in cases (22 out of 23), and two of them, A16V and R122H, likely fall on the C or risk haplotype of this locus (Table 7). Nonetheless, with only 19 A16V and R122H events in cases, these rare alleles cannot account for the association observed at this locus.

Sixty-nine control pancreas tissue samples from three sources were genotyped at rs10273639, and cDNA was used to quantify PRSS1 and control gene expression (Table 8). For all three sets of quantitative PCR data, the slope relating count of genotype C allele to PRSS1 expression level was positive; together, the samples provide evidence (p=0.01) that alleles at rs10273639 affect expression of PRSS1: expression levels were highest in patients with two C alleles at rs10273639, intermediate in heterozygotes, and lowest in subjects with two T alleles. Based on this evidence, we posit that reduced trypsinogen production protects the pancreas from injury, as has been observed in genetic mouse models[14].

Figure 11:
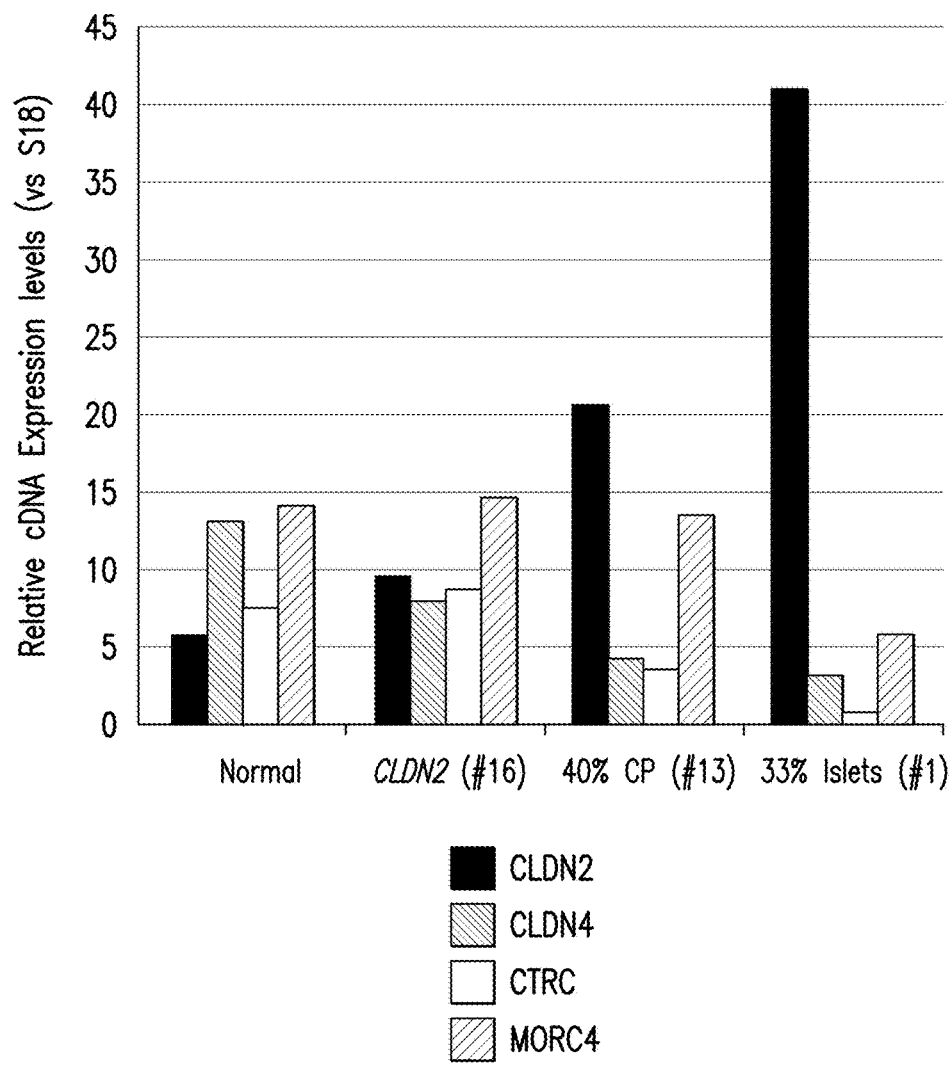
FIG. 11. Relative expression of CLDN2, CLDN4, CTRC, and MORC4 in control tissues. Surgical waste from grossly normal pancreas was collected and divided for histological, protein, and RNA studies. Relative expression of cDNA was analyzed with quantitative PCR using S18 RNA for normalization. Normal, average expression of 6 control samples with normal-appearing histology; CLDN2 genotyped as homozygous for rs12688220 A (control sample 16); 40% chronic pancreatitis (CP) on histological evaluation (control sample 13); and 33% islets on histological evaluation (control sample 1). Expression of CLDN2 appears to increase and CLDN4 to decrease with the high-risk CLDN2 genotype and in inflammation and islets, as expected[10,21,22]. CTRC is used as a marker of acinar cell gene expression, and MORC4 is another candidate gene within the CLDN2 locus. MORC4 expression does not correlate with CLDN2 expression or tissue histology.

CLDN2 is considered the primary candidate gene within our CLDN2 locus. Claudin-2 is attractive because it serves as a highly regulated tight junction protein forming low-resistance, cation-selective ion and water channels between endothelial cells[15,16] and is normally expressed at low levels between cells of the pancreatic ducts and in pancreatic islets[17,18]. The CLDN2 promoter includes an NFκB binding site[19], and gene expression is enhanced in other cells under conditions associated with injury or stress[20-22]. Claudin-2 can also be expressed by acinar cells when stressed, as reported in porcine models of acute pancreatitis[23]. Other genes within the CLND2 locus include MORC4, RIPPLY1, and TBC1D8B. MORC4 is expressed at low levels in most tissues, including the pancreas, with higher levels in the placenta and testis[24]. The MORC4 protein contains a CW four-cysteine zinc-finger motif, nuclear localization signal, and nuclear matrix-binding domain, suggesting that it may be a transcription factor[24], but its expression does not appear to correlate with pancreatitis (FIG. 11). RIPPLY1 and TBC1D8B are not known to be expressed in the pancreas.

To our knowledge, genetic variations in CLDN2 have not been associated with disease in humans. We assessed DNA sequence variants around CLDN2, RNA, and protein expression for claudin-2 in control tissue classified by histology and genotype (Table 9, FIG. 12). Evaluating 1000 Genomes data, no exonic variation was identified that could explain the association signal. Using materials and methods described previously for PRSS1 expression, CLDN2 expression levels in control tissues did not correlate with the CLDN2 locus risk genotype (p-value=0.32). Protein was extracted from the tissue, and only one protein band of the appropriate size was observed with anti-claudin-2 antibodies on Western blot, which correlated with tissue inflammation as determined by systematic grading of histology in adjacent tissue (FIG. 2A, FIG. 12). Immunohistochemical staining with anti-claudin-2 antibodies was verified in normal tissue (FIG. 2B), with kidney, duodenum, and bile ducts serving as additional positive controls (not shown). Protein localization was assessed in 12 GWAS cases who underwent pancreatic surgery: 6 with the CLDN2-containing high-risk genotype and 6 without. Claudin-2 cytoplasmic granular staining was markedly increased in both duct and acinar cells in chronic pancreatitis cases (FIG. 2C-E). Only chronic pancreatitis cases with the high-risk CLDN2 genotype demonstrated moderate-to-strong claudin-2 staining along the basolateral membrane of acinar cells (FIG. 2D, 2E, Table 9). Claudin-2 was also expressed in macrophages, which could contribute to the pathologic inflammatory process[25] (FIG. 2C, F).

Most studies report excessive alcohol consumption as the major risk factor for adult-onset chronic pancreatitis[26-29]. However, only 3% of patients who are alcoholics develop chronic pancreatitis[30], suggesting a pancreas-targeting risk factor. We compared genotypes based on whether pancreatitis was alcohol-related (yes/no)[5,31]. Setting control genotypes counts as the baseline category to be compared with case genotypes, the jointly estimated odds ratios for cases with a positive alcohol-related pancreatitis was greater for both rs10273639 (PRSS1-PRSS2 locus) and rs12688220 (CLDN2 locus) than those estimated for cases with a negative alcohol-related pancreatitis (Table 3). Thus, the effects of both loci appeared to be amplified by alcohol consumption. In a case-only analysis, both loci appear to interact with alcohol-related pancreatitis (Table 3), the CLDN2 locus most prominently (p-value=$4 \times 10^{-7}$).

We conclude that a common allele in the PRSS1-PRSS2 locus is associated with lower PRSS1 gene expression and that this effect is independent of the previously reported rare gain-of-function PRSS1 variants that increase susceptibility to both recurrent acute pancreatitis and chronic pancreatitis[8]. For this reason, and because risk variants at the PRSS1-PRSS2 locus exert a similar effect in patients with recurrent acute pancreatitis or chronic pancreatitis, it is reasonable to conjecture that variation at rs10273639 or variation in linkage disequilibrium with it directly affects risk for chronic pancreatitis and recurrent acute pancreatitis through its impact on trypsinogen expression. Variation at the CLDN2 locus, however, is much more strongly associated with chronic pancreatitis than recurrent acute pancreatitis, suggesting that it likely acts as a disease modifier to accelerate transition from recurrent acute pancreatitis to chronic pancreatitis. The significant association of the CLDN2 locus with alcohol suggests that the high-risk allele in the CLDN2 locus may modify risk through a non-trypsin-dependent process. Thus, we have characterized two common genetic risk modifiers for sporadic and alcohol-related chronic pancreatitis.

Protein-Protein and System-Based Interactions Among Genes with Variants Associated with Recurrent Acute and Chronic Pancreatitis.

The primary protein-protein interactions related to pancreatic disease involve trypsin (PRSS1) interacting with chymotrypsin C (CTRC) and pancreatic secretory trypsin inhibitor (SPINK1). When activated by trypsin, Chymotrypsin C degrades trypsin in low calcium environments (e.g., within the pancreatic acinar cell), thereby protecting the pancreas from premature trypsin activation[45,46]. Pancreatic secretory trypsin inhibitor is an acute phase protein (markedly up regulated by inflammation) and is a suicide inhibitor of trypsin[47,48].

Other protein-protein interactions are higher order, and their effects are indirect. For example, the pancreatic duct cells protect the pancreas from trypsin injury by secreting a bicarbonate-rich fluid using a CFTR-dependent mechanism to flush active trypsin out of the pancreas. Mild-variable mutations in the cystic fibrosis gene (i.e., CFTR) result in failed bicarbonate secretion, which results in a pH within the duct lumen that is favorable for trypsin activation. Recurrent trypsin activation results in injury and inflammation, which is countered by increased SPINK1 expression and the protection thus conferred. Genetic variants in SPINK1 limit the protection from premature trypsin activation, resulting in ongoing injury and the development of chronic pancreatitis over time. Thus, mild-variable CFTR variants are associated with chronic pancreatitis when they occur together with SPINK1 mutations, and vice versa, even though the proteins do not interact directly[49]. Similarly, the calcium sensing receptor (CASR) is located on the luminal side of the duct and monitors calcium concentrations[50]. When activated, CaSR, a G-coupled receptor, initiates a second messenger signal that opens CFTR to flush the duct and reduce calcium concentrations to limit trypsin-activation[45].

In Example 1, we hypothesize that a relative reduction of PRSS1 expression reduces the amount of trypsinogen in the pancreas and in turn reduces risk of activation, as is observed in genetic mouse models[51]. The other protein, claudin-2, is expected to act in parallel with CFTR in the duct. CFTR facilitates bicarbonate (HCO3-) secretion into the duct lumen through the duct cell; claudin-2 facilitates transport of sodium (Na+) and water between the ductal epithelial cells (paracellular flow)[52,53]. The sodium and bicarbonate meet within the duct to produce pancreatic juice. Thus, claudin-2 and CFTR do not directly interact, but their functions are intimately linked. Of note, claudin-2 is also up-regulated during inflammation[54-56], and we hypothesize that it is the abnormal regulation and localization of claudin-2 in response to injury and inflammation in patients with the high-risk CLDN2-locus genotype that leads to chronic pancreatitis. This hypothesis will be further studied to demonstrate that the mechanism is linked to the well-documented role of macrophages[57]. We identified claudin-2-positive macrophages, as well as claudin-2-positive acinar cells, in patients with the high-risk CLDN2 genotype (FIGS. 2 C&F) and speculate is the presence of a pathologic interaction, as proposed by others[58].

TABLE 1

Characterization of case subjects used for GWAS*.

| | | chronic pancreatitis | recurrent acute pancreatitis | chronic pancreatitis + recurrent acute pancreatitis |
|---|---|---|---|---|
| Stage 1 | | 676 | — | 676 |
| Alcohol-related pancreatitis[†] | Yes | 264 | — | 264 |
| | No | 411 | — | 411 |
| | Unknown | 1 | — | 1 |
| Stage 2 | | 331 | 579 | 910 |
| Alcohol-related pancreatitis[†] | Yes | 70 | 113 | 183 |
| | No | 256 | 462 | 718 |
| | Unknown | 5 | 4 | 9 |
| Combined | | 930 | 579 | 1506 |
| Alcohol-related pancreatitis[†] | Yes | 334 | 113 | 447 |
| | No | 667 | 462 | 1129 |
| | Unknown | 6 | 4 | 10 |

*Does not include information from controls in Stage 1 (n = 4514) or from Stage 2 (n = 4053). For more complete characterization of samples, please see Table 4 in the Appendix.
[†]Alcohol-related pancreatitis was assigned by the study physician at enrollment.

TABLE 2

Results for leading SNPs at the PRSS1-PRSS2 and CLDN2 loci from Stage 1, Stage 2, and joint analysis.

| | | | | | CP + RAP Allele Frequency (A1) | | CP Stage 1 | | | CP + RAP Stage 2 | | | CP + RAP Combined | | |
|---|---|---|---|---|---|---|---|---|---|---|---|---|---|---|---|
| CHR | SNP | BP | A1* | A2 | cases | controls | OR | se(OR) | P | OR | se(OR) | P | OR | se(OR) | P |
| 7 | rs10273639 | 142456928 | T | C | 0.350 | 0.424 | 0.712 | 0.044 | $3.0 \times 10^{-8}$ | 0.748 | 0.039 | $7.5 \times 10^{-8}$ | 0.734 | 0.029 | $2.0 \times 10^{-14}$ |
| X | rs7057398 | 106144529 | C | T | 0.374 | 0.281 | 1.493 | 0.075 | $1.4 \times 10^{-15}$ | 1.210 | 0.066 | $1.8 \times 10^{-5}$ | 1.321 | 0.049 | $4.6 \times 10^{-17}$ |
| X | rs12688220 | 106244767 | T | C | 0.367 | 0.261 | 1.612 | 0.081 | $2.4 \times 10^{-21}$ | 1.238 | 0.073 | $2.3 \times 10^{-6}$ | 1.385 | 0.054 | $2.3 \times 10^{-22}$ |

*A1 is the allele counted for purposes of computing odds ratio and associated statistics. The model used here includes covariates to control for the two leading eigenvectors for ancestry, as was done in the Plink analyses, but differs in its treatment of the minor allele count for the CLDN2 locus, which resides on the X chromosome (as described in Online Methods). Alleles given are refSNP alleles according to dbSNP. See Table 5 for all SNPs passing quality control and showing p-value $<5 \times 10^{-7}$ for Stage 1 or Stage 2 or the joint analysis.

TABLE 3

Allele frequencies for rs10273639 (risk allele C) and rs12688220 (risk allele T) when data are stratified by controls or pancreatitis ± alcohol-related diagnosis.

| Status | Alcohol-related | Number of individuals | rs10273639[1] (C) frequency | rs12688220[1] (T) frequency |
|---|---|---|---|---|
| Control | — | 8029 | 0.576 | 0.261 |
| Pancreatitis | No | 1129 | 0.634 | 0.322 |
| Pancreatitis | Yes | 447 | 0.696 | 0.427 |

[1] Using data from cases only and in a joint analysis of both SNPs, rs12688220 predicts alcohol-related pancreatitis as genotypes ($\chi2 = 29.57$; DF = 2; p-value = $4 \times 10^{-7}$) or count of risk alleles ($\chi2 = 13.17$; DF = 1; p-value = $3 \times 10^{-4}$). rs10273639 (PRSS1-PRSS2 locus) is a significant predictor (count of risk alleles: $\chi2 = 5.68$; DF = 1; p-value = 0.017; genotypes: $\chi2 = 6.05$; DF = 2; p-value = 0.049), even after accounting for the effects of rs12688220.

TABLE 4

Demographic characteristics of pancreatitis patients and controls (see footnote[1] for details of recruitment).

| Study | n | male | female | Age mean | Age sd |
|---|---|---|---|---|---|
| Chronic Pancreatitis | | | | | |
| ALL | 930 | 501 | 429 | 48.6 | 17.0 |
| German | 150 | 84 | 66 | 39.9 | 15.9 |
| HP | 53 | 19 | 34 | 35.9 | 19.4 |
| Milwaukee | 45 | 30 | 15 | 61.8 | 15.4 |
| NAPS-CV | 275 | 150 | 125 | 51.7 | 15.3 |
| NAPS2 | 406 | 217 | 189 | 49.7 | 16.2 |
| PAGER | 1 | 1 | | 54.0 | |
| Recurrent Acute Pancreatitis | | | | | |
| ALL | 576 | 247 | 329 | 44.4 | 16.5 |
| German | 91 | 38 | 53 | 40.2 | 16.9 |
| HP | 30 | 11 | 19 | 32.8 | 20.6 |
| Milwaukee | 25 | 4 | 21 | 52.3 | 15.9 |
| NAPS-CV | 53 | 29 | 24 | 43.7 | 14.6 |
| NAPS2 | 373 | 163 | 210 | 45.9 | 15.8 |
| PROOF | 2 | 1 | 1 | 33.0 | 4.2 |
| SAPS | 2 | 1 | 1 | 62.5 | 7.8 |
| Control | | | | | |
| ALL | 538 | 213 | 325 | 55.1 | 15.7 |
| NAPS-CV | 10 | 4 | 6 | 46.1 | 11.4 |
| NAPS2 | 386 | 149 | 237 | 53.9 | 14.9 |
| PAGER | 10 | 2 | 8 | 66.2 | 13.7 |
| Somalogic | 132 | 58 | 74 | 58.4 | 17.3 |

Figure 4:
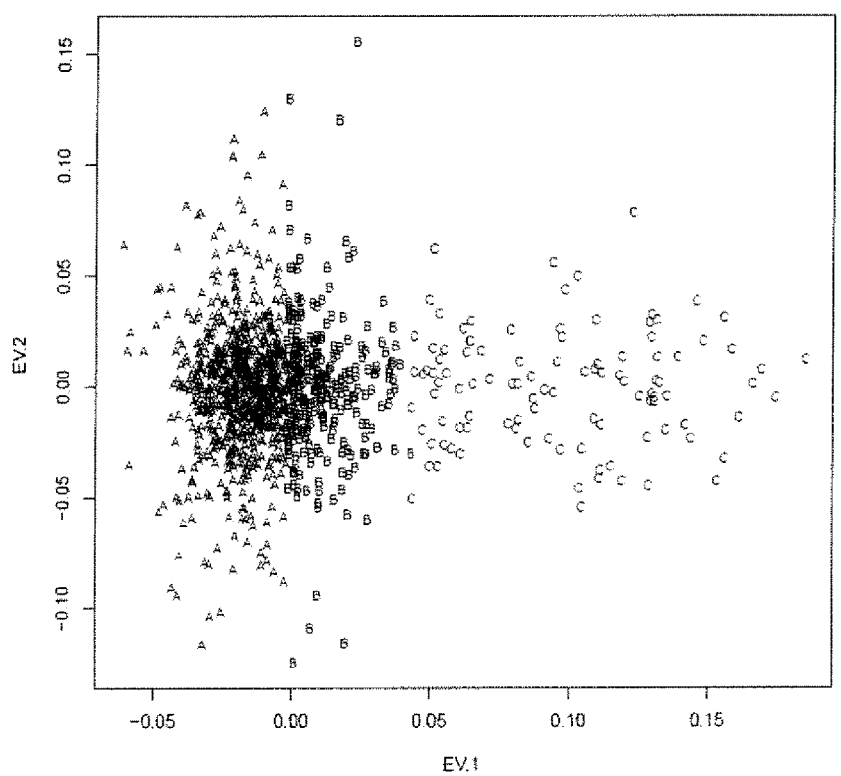
FIG. 4. Results from genetic ancestry analysis for chronic pancreatitis cases. dacGem (http://arxiv.org/abs/1104.1162) was used to convert multi-locus genotypes to ancestry dimension, expressed as eigenvectors. The decomposition resulted in a single significant dimension representing ancestry. Letters indicate ancestrally homogeneous clusters; of these clusters A and B are taken to represent a relatively homogeneous European ancestry. Note there was only one significant dimension of ancestry identified, although two are shown here.
Figure 5:
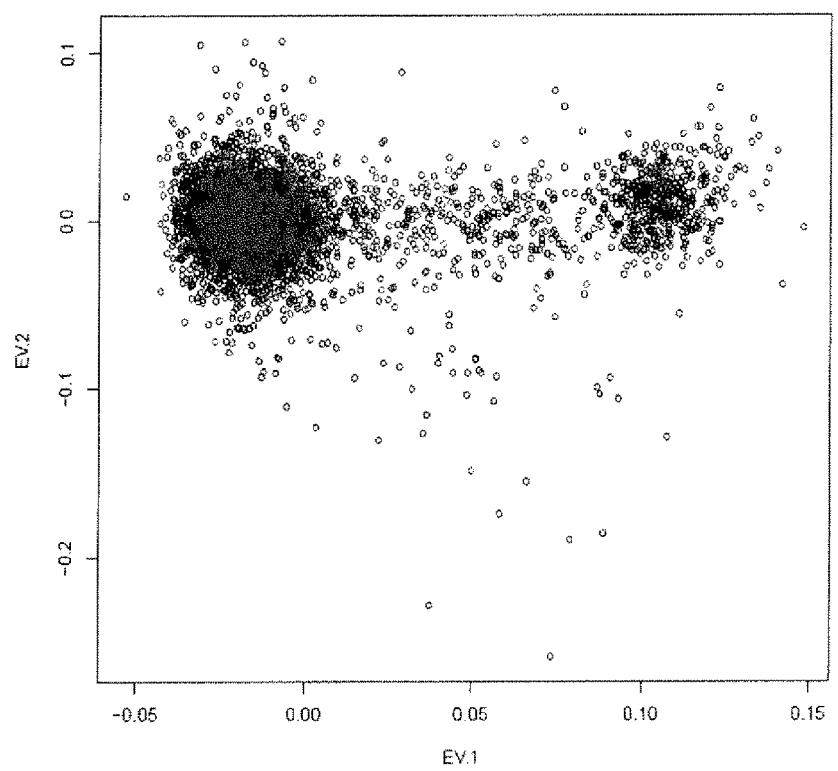
FIG. 5. Results from genetic ancestry analysis for chronic pancreatitis cases and ADGC controls. dacGem (http://arxiv.org/abs/1104.1162) was used to convert multi-locus genotypes to ancestry dimension, expressed as eigenvectors. The decomposition resulted in a single significant dimension representing ancestry. Red symbols are cases, blue symbols are controls. Note there was only one significant dimension of ancestry identified, although two are shown here.

[1] The study included case and control samples of European ancestry, which was also validated genetically (FIGS. 3 & 4). The North American Pancreatitis Study 2 (NAPS2) prospectively ascertained and phenotyped 540 chronic pancreatitis (CP) patients, 460 recurrent acute pancreatitis (RAP) patients, and 695 control subjects from 20 US expert clinical centers between August 2000 and September 2006 as described[59]. The NAPS2 continuation and validation study (NAPS2-CV) ascertained an additional 516 CP patients through March 2012. Parallel studies at the University of Pittsburgh that used the same NAPS2 case report forms and methods included the Severity of Acute Pancreatitis Study/Pancreatitis-associated Risk of Organ Failure (SAPS/PROOF) study[60] (Papachristou, PI), which ascertained RAP patients between June 2003 until March 2012; and the Pancreatic Adenocarcinoma Gene-Environment Risk (PAGER) study[62] (Brand, PI), ascertained controls between February 2002 and March 2012. Only Caucasian cases and controls that met NAPS2 criteria for RAP, CP, or control were included. Cases from the Hereditary Pancreatitis (HP) study[62] (Whitcomb, PI) were primarily probands of small familial pancreatitis families or spouses of affected individuals as controls. DNA samples from Milwaukee were obtained from Aurora Health Care system, Saint Luke's Hospital, Milwaukee, WI, as part of the Open-Source Robotic Biorepository & Information Technology (ORBIT) program (Tector, Director) using de-identified DNA samples and case forms completed by an honest broker using electronic medical records. Liverpool samples were collected as clinical referrals (Neoptolemos, PI), while the German samples were prospectively collected from clinical visits and referrals centered in Munster, DE and Greifswald, DE (Lerch, PI). Additional phenotyped Caucasian control DNA samples were provided in collaboration with SomaLogic, Inc (Boulder CO). Alzheimer Disease Genetics Consortium (ADGC) samples consisted of cases and controls genotyped on the Illumina HumanOmniExpress Beadchips and judged to be of European ancestry by genetic analysis[63]. The NeuroGenetics Research Consortium (NGRC[64]) collected a set of 2000 cases and 2000 controls for the Genome-Wide Association Study of Parkinson Disease: Genes and Environment. These samples, which were used as controls for the Stage 2 GWAS, were genotyped on the Illumina 1M. Data from these samples are obtained from dbGaP Study Accession: phs000196.v2.p1 (http://www.ncbi.nlm.nih.gov/projects/gap/cgi-bin/study.cgi?study_id = phs000196.v2.p1), where a detailed study description can be found. These subjects are consented for general use genetics studies.

TABLE 5

SNPs from Stage 1, Stage 2, and the joint analysis (SNPs passing quality control, have p <5 x 10-7 for the Stage 1 or Stage 2 or combined analysis based on results from Plink).

| CHR | SNP | BP | A1* | A2 | CP + RAP Allele Frequency (A1) cases | CP + RAP Allele Frequency (A1) controls | CP Stage 1 OR | CP Stage 1 se(OR) | CP Stage 1 P | CP + RAP Stage 2 OR | CP + RAP Stage 2 se(OR) | CP + RAP Stage 2 P | CP + RAP Combined OR | CP + RAP Combined se(OR) | CP + RAP Combined P |
|---|---|---|---|---|---|---|---|---|---|---|---|---|---|---|---|
| 7 | rs10273639 | 142456928 | T | C | 0.350 | 0.424 | 0.712 | 0.044 | $3.0 \times 10^{-8}$ | 0.748 | 0.039 | $7.5 \times 10^{-8}$ | 0.734 | 0.029 | $2.0 \times 10^{-14}$ |
| 8 | rs11988997 | 119766194 | T | C | 0.094 | 0.071 | 1.086 | 0.120 | $4.6 \times 10^{-1}$ | 1.593 | 0.095 | $1.1 \times 10^{-7}$ | 1.359 | 0.074 | $6.1 \times 10^{-6}$ |
| 10 | rs2995271 | 30519832 | C | T | 0.196 | 0.238 | 0.780 | 0.058 | $7.8 \times 10^{-4}$ | 0.794 | 0.050 | $3.2 \times 10^{-4}$ | 0.789 | 0.038 | $8.2 \times 10^{-7}$ |
| X | rs379742 | 105493919 | T | C | 0.250 | 0.200 | 1.392 | 0.077 | $1.8 \times 10^{-9}$ | 1.076 | 0.070 | $1.5 \times 10^{-1}$ | 1.203 | 0.052 | $5.9 \times 10^{-7}$ |
| X | rs4409525 | 106140325 | A | G | 0.372 | 0.281 | 1.486 | 0.075 | $4.1 \times 10^{-15}$ | 1.195 | 0.066 | $6.4 \times 10^{-5}$ | 1.310 | 0.049 | $4.5 \times 10^{-16}$ |
| X | rs7057398 | 106144529 | C | T | 0.374 | 0.281 | 1.493 | 0.075 | $1.4 \times 10^{-15}$ | 1.210 | 0.066 | $1.8 \times 10^{-5}$ | 1.321 | 0.049 | $4.6 \times 10^{-17}$ |
| X | rs12008279 | 106160702 | G | A | 0.509 | 0.437 | 1.338 | 0.065 | $2.7 \times 10^{-9}$ | 1.126 | 0.056 | $4.9 \times 10^{-3}$ | 1.212 | 0.043 | $1.6 \times 10^{-9}$ |
| X | rs5917027 | 106162634 | C | T | 0.515 | 0.438 | 1.330 | 0.065 | $5.6 \times 10^{-9}$ | 1.158 | 0.056 | $4.9 \times 10^{-4}$ | 1.229 | 0.042 | $9.7 \times 10^{-11}$ |
| X | rs12014762 | 106183670 | T | C | 0.279 | 0.202 | 1.523 | 0.081 | $2.2 \times 10^{-15}$ | 1.182 | 0.075 | $6.5 \times 10^{-4}$ | 1.318 | 0.055 | $1.5 \times 10^{-14}$ |
| X | rs6622126 | 106200202 | A | G | 0.510 | 0.435 | 1.329 | 0.065 | $6.1 \times 10^{-9}$ | 1.154 | 0.056 | $6.8 \times 10^{-4}$ | 1.225 | 0.042 | $1.9 \times 10^{-10}$ |
| X | rs12688220 | 106244767 | T | C | 0.367 | 0.261 | 1.612 | 0.081 | $2.4 \times 10^{-21}$ | 1.238 | 0.073 | $2.3 \times 10^{-6}$ | 1.385 | 0.054 | $2.3 \times 10^{-22}$ |

*A1 is the allele counted for purposes of computing odds ratio and associated statistics. The model used here includes covariates to control for the two leading eigenvectors for ancestry, as was done in the Plink analyses, but differs in its treatment of the minor allele count for the CLDN2 locus, which resides on the X chromosome. In this case, Plink encodes the count of minor alleles in males as 0 and 1 and includes a sex effect; instead, following Clayton (2009; PMID: 19939292), we model the male genotypes as 0 and 2 and do not include the sex effect, because this is a more powerful approach. Alleles given are refSNP alleles according to dbSNP, which are not necessarily the alleles designated in the Illumina map.

TABLE 6

Odds ratios (OR), the standard error of the odds ratio (SE), and associated p-value, by Stage and diagnosis, for the most significant SNP at the PRSS1-PRSS2 locus and the CLDN2 locus.

| Dx | Data | PRSS1-PRSS2 locus rs10273639 (T allele) | | | CLDN2 locus rs12688220 (T allele) | | |
|---|---|---|---|---|---|---|---|
| | | OR* | se(OR) | p-value | OR | se(OR) | p-value |
| CP | Stage 1 | 0.713 | 0.044 | $3.0 \times 10^{-8}$ | 1.612 | 0.081 | $2.4 \times 10^{-21}$ |
| CP. RAP | Combined | 0.734 | 0.030 | $2.0 \times 10^{-14}$ | 1.385 | 0.046 | $2.3 \times 10^{-22}$ |
| CP | Stage 2 | 0.633 | 0.055 | $1.4 \times 10^{-7}$ | 1.336 | 0.092 | $2.6 \times 10^{-6}$ |
| CP | Combined | 0.683 | 0.034 | $1.7 \times 10^{-14}$ | 1.496 | 0.060 | $1.0 \times 10^{-23}$ |
| CP. RAP | Stage 2 | 0.745 | 0.040 | $7.5 \times 10^{-8}$ | 1.238 | 0.056 | $2.3 \times 10^{-6}$ |

*The model used here includes covariates to control for the two leading eigenvectors for ancestry, as was done in the Plink analyses, but differs in its treatment of the minor allele count for the CLDN2 locus, which resides on the X chromosome. In this case, Plink encodes the count of minor alleles in males as 0 and 1 and includes a sex effect; instead, following Clayton (2009; PMID: 19939292), we model the genotypes as 0 and 2 and do not include the sex effect, because this is a more powerful approach.

TABLE 7

Distribution of rare, exonic risk variants in PRSS1 by genotype at rs10273639 (C is risk allele for rs10273639). These results indicate that the N291 risk allele resides on the T haplotype of rs10273639 (non-risk), whereas the A16V and R122H alleles reside on the C haplotype (risk).

| Sequence variant | All individuals | | | All cases (CP + RAP) | | |
|---|---|---|---|---|---|---|
| | TT | CT | CC | TT | CT | CC |
| Wild Type | 151 | 505 | 459 | 84 | 337 | 325 |
| A16V | | 2 | 2 | | 2 | 1 |
| N29I | 1 | 2 | | 1 | 2 | |
| R122H | | | 8 | 8 | | 8 | 8 |

Results are from NAPS2 samples, which were analyzed for rare variants over the duration of the NAPS2 study; the method of DNA analysis varied over time. Three rare variants—A16V, N29I and R122H of PRSS1 (n=1112 with complete data on rare and common variant genotypes)—were evaluated by using a combination of methods, such as Surveyor (Transgenomic-Omaha, Nebr.) and Sequencing (Applied Biosystems-Carlsbad, Calif.). The first batch of 950 samples were screened for exonic base-pair changes by Surveyor, and all positive and randomly selected negative samples were confirmed by Sequencing (Big Dye Terminator v3.1 Cycle Sequencing Kit cat#4337456). All additional samples (n=665) were performed by Sequencing methods only. In brief, the Surveyor methodology (Surveyor Mutation Detection Kits cat #706020; http://www.transenomic.com/pd/surveyorSurveyor.asp) uses four steps: PCR amplification of DNA from wild-type and unknown sequence, followed by a hybridization step that forms hetero- and homo-duplexes, after which an enzyme that cuts at mismatched nucleotides is added, and finally DNA fragments are size-separated by gel electrophoresis.

We also validated genotypes of rs10273639 by independent TaqMan genotyping two SNPs in linkage disequibrium with it—rs2011216, in intron 1 of PRSS1, and rs6667, synonymous variant in exon 5 of PRSS1—in 1158 NAPS2 case and control subjects with complete SNP data. For all but 2 of the 1158 samples (99.83%), rs10273639 TaqMan genotypes were identical to those from OmniExpress. Alleles of the synonymous variant rs6667 were in perfect linkage disequilibrium with those at rs10273639, whereas alleles at rs2011216 showed a modest departure (data not shown). These results provide independent validation of rs10273639 genotypes, thereby confirming their association with risk for pancreatitis (FIG. 1), and identify other SNPs that would produce genomewide association, including a synonymous SNP.

TABLE 8

Normalized gene expression from pancreatic tissue for PRSS1, PRSS2, and CLDN2. Genotypes for rs10273639 (PRSS1-PRSS2 locus) and rs12688220 (CLDN2 locus) are given in the last two columns.

| Study | ID | PRSS1 | PRSS2 | CLDN2 | rs10273639 | rs12688220 |
|---|---|---|---|---|---|---|
| PITT | A | 0.218 | 0.029 | NA | TT | NA |
| PITT | B | 0.218 | 0.090 | NA | CT | NA |
| PITT | C | 0.797 | 0.029 | NA | CT | NA |
| PITT | D | 0.877 | 0.593 | NA | CT | NA |
| PITT | E | 0.840 | 0.557 | NA | CT | NA |
| PITT | F | 1.657 | 1.319 | NA | CC | NA |
| PITT | G | 0.593 | 0.213 | NA | CC | NA |
| PITT | H | 1.459 | 1.470 | NA | CC | NA |
| PITT | I | 0.738 | 0.598 | NA | CC | NA |
| PITT | J | 0.914 | 0.670 | NA | CC | NA |
| PSU | XBB 048 | 0.426 | 1.437 | 3.778 | CT | TT |
| PSU | XBH 221 | 3.160 | 1.913 | 2.333 | CT | CC |
| PSU | XBW 333 | 3.320 | 1.832 | 4.823 | CC | TT |
| PSU | XEY 176 | 0.326 | 0.479 | 3.773 | CT | CC |
| PSU | XFA 462 | 0.267 | 0.422 | 1.505 | CT | TT |
| PSU | XFU 215 | −0.238 | 0.296 | 2.690 | TT | TT |
| PSU | XFY 110 | −2.912 | −2.752 | −0.368 | TT | TT |
| PSU | XGE 449 | 0.000 | 0.000 | 0.000 | TT | CT |
| PSU | XGI 233 | 0.017 | 0.065 | 0.792 | CC | TT |
| PSU | XHI 170 | 1.304 | 1.172 | −4.853 | CT | CC |
| PSU | XHN 379 | −0.010 | 0.610 | −1.307 | TT | TT |
| PSU | XHN 423 | −0.052 | −1.155 | −7.175 | CC | TT |
| PSU | XIG 483 | 0.305 | 0.522 | 2.495 | CT | CC |
| PSU | XIW 265 | 1.204 | 1.494 | 3.844 | CT | TT |
| PSU | XJ 1285 | 3.524 | 2.351 | 4.950 | CC | TT |
| PSU | XJD 339 | −0.977 | 0.137 | −6.026 | CT | CC |
| PSU | XJD 439 | 0.041 | 0.449 | 2.159 | NA | TT |

TABLE 8-continued

Normalized gene expression from pancreatic tissue for PRSS1, PRSS2, and CLDN2. Genotypes for rs10273639 (PRSS1-PRSS2 locus) and rs12688220 (CLDN2 locus) are given in the last two columns.

| Study | ID | PRSS1 | PRSS2 | CLDN2 | rs10273639 | rs12688220 |
|---|---|---|---|---|---|---|
| PSU | XJD 447 | 2.479 | 2.729 | −4.003 | CT | TT |
| PSU | XJG 039 | −0.134 | −0.565 | −6.244 | CC | TT |
| PSU | XJG 404 | 1.255 | 1.183 | 2.412 | CT | TT |
| PSU | XJH 462 | 2.220 | 0.885 | 2.149 | CT | TT |
| PSU | XKB 098 | −1.023 | −1.355 | −6.190 | TT | CC |
| PSU | XKD 006 | 0.224 | 0.484 | 3.697 | NA | TT |
| PSU | XKF 331 | 0.858 | 0.732 | 1.997 | TT | TT |
| PSU | XKR 071 | 1.103 | 0.632 | 4.126 | CT | TT |
| PSU | XKU 176 | 3.893 | 2.218 | 1.277 | CT | CC |
| PSU | XL2098 | 2.698 | −0.128 | −3.505 | CT | TT |
| PSU | XLE 240 | 4.046 | 3.805 | −3.703 | CT | CC |
| PSU | XLT 278 | 3.504 | 4.232 | −2.162 | CT | CC |
| PSU | YAC 312 | 0.399 | 1.769 | 3.485 | TT | CC |
| PSU | YC 3158 | −0.442 | 0.457 | 2.493 | CT | TT |
| PSU | YC 4332 | NA | 1.623 | 3.303 | TT | CC |
| PSU | YCC 461 | 2.403 | 0.979 | 1.647 | CT | CT |
| PSU | YCH 191 | −0.162 | 0.254 | 0.824 | TT | CC |
| PSU | YCM 298 | 1.825 | 1.495 | 2.549 | TT | TT |
| PSU | YCW 158 | 1.734 | 1.074 | 4.267 | CC | TT |
| PSU | YCX 167 | 0.199 | 0.704 | 1.426 | NA | TT |
| PSU | YCX 238 | 4.861 | 3.973 | 3.444 | CT | TT |
| PSU | YDI 386 | 0.557 | 0.867 | 0.552 | CT | TT |
| PSU | YDJ 130 | 0.077 | 0.434 | 2.690 | CC | CT |
| PSU | YDX 455 | 0.069 | 0.941 | 5.515 | CT | CC |
| PAGER | PA1318 | −2.150 | −2.380 | NA | TT | CT |
| PAGER | PA1509 | 0.741 | −1.936 | −8.583 | CC | CT |
| PAGER | PA1527 | −0.510 | −2.106 | NA | CT | TT |
| PAGER | PA1553 | −1.640 | −2.622 | NA | TT | TT |
| PAGER | PA1566 | 1.813 | −1.743 | −20.035 | CT | TT |
| PAGER | PA1601 | −0.436 | −0.748 | NA | CT | CC |
| PAGER | PA1615 | −0.361 | 0.045 | −0.855 | TT | CT |
| PAGER | PA1641 | −0.696 | −1.011 | −1.470 | CT | CT |
| PAGER | PA1683 | −0.128 | 0.035 | 2.255 | CC | CT |
| PAGER | PA1690 | 0.000 | 0.000 | 0 | CT | CT |
| PAGER | PA1701 | −0.881 | −0.775 | −3.279 | CC | TT |
| PAGER | PA1714 | −0.316 | −1.861 | −2.993 | TT | TT |
| PAGER | PA1728 | −0.697 | −1.056 | −3.328 | TT | CT |
| PAGER | PA1742 | −0.798 | −1.096 | NA | CT | TT |
| PAGER | PA1761 | −1.365 | −2.529 | 2.756 | TT | CC |
| PAGER | PA1796 | −0.560 | −2.208 | NA | TT | CT |
| PAGER | PA1824 | 0.040 | −1.270 | 0.298 | TT | TT |
| PAGER | PA1855 | −0.384 | 0.125 | NA | TT | CT |
| PAGER | PA1880 | −1.968 | −1.490 | NA | CT | CT |
| PAGER | PA1893 | −2.351 | −2.745 | NA | CT | TT |
| PAGER | PA1900 | −1.291 | −0.568 | NA | CT | CT |
| PAGER | PA1959 | −0.896 | −1.613 | −4.529 | CT | TT |

"Study" refers to the source of each of 3 sets samples analyzed, "ID" distinguishes subject sample, and NA means not available.

To determine whether PRSS1 or CLDN2 gene expression was associated with SNP genotypes (rs10273639 and rs12688220 respectively), we fit the normalized gene expression to counts of alleles. For rs10273639 (PRSS1 locus), the count of alleles is 0, 1, or 2 C for risk alleles, whereas for rs12688220 (CLDN2 locus), we used the allele encoding described in the footnote of Table 5 (0/2 for males) with T being the risk allele. We fit the data for the three studies separately and then combined the results to form a single test statistic using a weighted sum of z-statistics, with the weights determined by sample size.

For PRSS1 expression, the 3 slopes were 0.414±0.1809 (±se); 0.756±0.4094; and 0.301±0.2904, with z-values 2.29, 1.85, and 1.04, which yields an overall p-value of 0.0099. (We removed 2 outliers, an observation with value<−4 from PAGER and one from PSU with value>9.) For CLDN2 expression, only 2 sample sets were characterized; the 2 slopes were −0.636±0.5943 and 0.205±1.4804, and z-values were −0.651 and 0.022, which yields an overall p-value of 0.32. (We removed one outlier from PAGER with value<−15.)

TABLE 9

Histology and anti-claudin-2 staining of chronic pancreatitis tissue in GWAS cases.
The samples are divided by rs12688220 genotype (1-2, low risk; = 7-12 high risk).

| | Claudin-2 staining | | | | | | | | |
|---|---|---|---|---|---|---|---|---|---|
| | Intact acinar Cells | | Atrophic acinar cells | | Terminal ducts | | Intralobular ducts | | |
| Histology | Cytoplasm (granular) | membrane | Cytoplasm (granular) | membrane | Cytoplasm (granular) | membrane | Cytoplasm (granular) | membrane | Islets |
| Low-risk genotypes | | | | | | | | | |
| 1 increased fibrosis, some residual lobules, some atrophy, chronic inflammation with lymphoid aggregates | ++ | − | ++ | − | +++ | − | +++ | − | + |
| 2 residual acini, increased fibrosis, mild chronic inflammation | ++ | + | ++ | − | ++ | − | +++ | − | ++ |
| 3 residual acini with mild chronic inflammation; multifocal acute inflammation (?type 2 AIP?) | ++ | + | ++ | − | +++ | − | +++ | − | NP |
| 4 atrophic, fibrotic, chronic inflammation | ++ | | +++ | | +++ | − | NP | | NP |
| 5 lots of fibrosis, mild chronic inflammation, some residual intact and atrophic lobules | ++ | + | ++ | − | +++ | − | +++ | −/+ | ++ |
| 6 intact lobules, increased fibrosis, mild chronic inflammation | ++ | − | ++ | − | ++ | − | +++ | −/+ | ++ |
| High-risk genotype | | | | | | | | | |
| 7 mostly atrophic with fibrosis and chronic inflammation | + | +++ | − | P +++ | ++/+++ | − | ++/+++ | f | ++ |
| 8 increased fibrosis, some atrophy | − | +++ | + | ++++ | +/++ | − | na | | NP |
| 9 patchy chronic pancreatitis; mostly preserved | ++ | p ++ | ++ | − | +++ | − | +++ | − | ++ |
| 10 increased fibrosis, atrophy, rare residual lobule | ++ | P ++ | ++ | − | +++ | − | +++ | − | +++ |
| 11 increased fibrosis, atrophy, rare residual lobule | ++ | P ++ | ++ | − | ++ | − | ++ | − | ++ |
| 12 increased fibrosis, atrophy, rare residual lobule | ++ | P ++ | ++ | − | ++ | − | ++ | − | ++ |

"Staining intensity scale of − to ++++ (−, negative; +, weak; ++, moderate; +++, strong); f, focal; P, patchy; NP, structure was not present in the tissue section. The section in rows 7-12 of column 3 identifies the primary feature that differentiates claudin-2 staining based on CLDN2 genotype."

Methods

Subject Recruitment:

Details of recruitment of cases and controls are reported in Table 4. All studies were conducted under institutional review board-approved protocols.

Stage 1 Samples:

All N=758 Stage 1 case samples were from the North American Acute Pancreatitis Study (NAPS2[5]) were diagnosed with chronic pancreatitis, and were characterized for alcohol-related pancreatitis (Table 1). chronic pancreatitis occurs in less than 0.05% of the population, so a convenience sample provides essentially identical power as a same-sized sample of controls selected for the absence of chronic pancreatitis[32]. For controls, we used genotypes from 4076 cases and controls from the Alzheimer Disease Genetics Consortium (ADGC) and 493 NAPS2 subjects, all genotyped on the same platform as the chronic pancreatitis samples.

Stage 2 Samples:

The Stage 2 samples consisted of N=343 chronic pancreatitis and N=627 recurrent acute pancreatitis cases (Table 1, Table 4) as well as 4191 control subjects (3986 from the NeuroGenetics Research Consortium, NGRC, and 205 NAPS2 controls).

Genotypes:

All cases and NAPS2 controls were genotyped by the University of Pittsburgh Genomics and Proteomics Core Laboratories using the Illumina HumanOmniExpress Beadchip. Samples were processed and scanned using the manufacturer's recommended protocols with no modifications. ADGC samples[33] were also genotyped using Illumina HumanOmniExpress Beadchips, whereas NGRC samples[34] were genotyped on the Illumina Human1M-Duo DNA Analysis BeadChip.

Quality Control (QC) for Stage 1:

QC was performed for individuals and then SNPs to determine which samples and SNPs should not be included in the analysis ("dropped"). Assessing sex miscalls based on X chromosome genotypes using Plink[35], 7 chronic pancreatitis cases and 20 controls (10 NAPS2; 10 ADGC) were dropped. Based on the requirement for ≥95% complete genotypes per individual, 40 cases and 27 controls (20 NAPS2 controls and 7 ADGC controls) were dropped. Searching duplicate or highly related samples based on genotype and using GCTA software[36] (Genetic Relationship Matrix score GRM>0.4), 35 cases and 78 controls (2

NAPS2, 76 ADGC) were dropped. After these QC filters, 676 cases and 4507 controls remained for association analysis.

SNP QC was first performed using NAPS2 and ADGC samples separately. Ancestry was estimated using dacGem[37] based on 9700 SNPs that had a genotype completion rate of ≥99.9%, a minor allele frequency MAF≥0.05, and were separated by at least 500 Kb. Analysis of genotypes from NAPS2 subjects identified 1 significant dimensions of ancestry and clustered subjects into 3 groups (FIG. 3). Groups A and B, illustrated in FIG. 3, delineate 764 and 282 subjects, respectively, of European ancestry (self-identified); SNP QC for MAF and Hardy Weinberg Equilibrium (HWE) were performed on data from these subjects. Of 731,442 SNPs received, 633,790 passed QC filters. SNPs were dropped for the following reasons: 3165 for map location; 11,977 for call rate; 77,300 for MAF<0.01; and 5219 failed HWE (p-value<0.005).

ADGC data were received in three waves of 1763, 1110, and 1266 subjects. In the first wave, 659,224 SNPs were received, while in waves two and three, 730,525 SNPs were received. After QC as described for the chronic pancreatitis cohort, including harmonization with SNPs passing QC in the chronic pancreatitis cohort, 604,059, 632,761, and 633,023 SNPs remained, respectively. After merging cohorts, 30 related subjects were dropped, leaving 4046 ADGC subjects. Of the 633,615 unique SNPs in this ADGC, QC filters dropped 5 for low MAF and 5316 for HWE, leaving 628,294 SNPs. Combining ADGC and chronic pancreatitis cohorts and performing another round of QC yielded 625,739 SNPs for analysis.

QC for Stage 2:

QC for individuals was performed as described for Stage 1. These individual-specific QC filters removed 60 cases, leaving 331 chronic pancreatitis and 579 recurrent acute pancreatitis cases for analysis; 14 controls were also removed, leaving 4177 controls for analysis. We analyzed all SNPs passing QC at Stage 1.

Association Analysis:

To control confounding due to ancestry, the first 10 major eigenvectors from the spectral decomposition were used as covariates in Stage 1 and Stage 2 analyses[38], although only one was significant. We contrasted the genotypes of case subjects and controls via logistic regression and a log-additive (log it) model using Plink[35]. Genotypes for any SNPs showing association p-value<$5\times10^{-7}$ were manually inspected for valid genotype clustering. SNPs showing poor-quality clustering were excluded. Following Skol et al.[7] and others, we take an overall significance level of $5\times10^{-8}$ and $5\times10^{-7}$ for strongly suggestive association.

To determine whether alcohol interacts with genetic variation to alter risk of pancreatitis, data from cases were fit to a general linear model in which count of alleles or genotypes predicted alcohol etiology (yes/no). The test statistic was obtained as a likelihood ratio chi-square. Note that in these analyses and any analyses other than genomewide association, we model the male genotypes as 0 and $2^{39,40}$. For the genomewide association, Plink encodes the count of minor alleles in males as 0 and 1 and includes a sex effect, but the 0/2 encoding for males is a more powerful approach[39,40].

DNA Extraction:

DNA was obtained using standard methods[41].

Pancreatic Tissue Processing:

Tissue was obtained from two sources [Pitt and Pancreatic Adenocarcinoma Gene-Environment Risk (PAGER) from the University of Pittsburgh and PSU from Pennsylvania State University] and processed in three batches: banked (Pitt) and prospectively collected (PAGER) surgical waste from uninvolved pancreas and normal pancreas specimens from the Gift of Life Program that were not used for transplantation (PSU). PAGER samples were snap-frozen, placed in RNAlater solution (Ambion), and stored at −80° C. PSU pancreas samples were also snap frozen and preserved in formalin or placed in RNAlater solution. RNA was isolated using Trizol reagent (Invitrogen), and its quality examined in 1% agarose gel stained with ethidium bromide. cDNA was transcribed using oligo dt primers and the Superscript II reverse transcriptase kit (Invitrogen).

Gene Expression:

Relative expression of PRSS1, PRSS2, CTRC, and 18S was determined by analyzing cDNA using Taqman®-based rtPCR assays (Applied Biosystems). Raw absolute quantitation results were analyzed and converted to relative expression results by software packages SDS V2.3 and DataAssist V1.0 (Applied Biosystems). Assays were repeated in triplicate or quadruplicate. Three sets of samples were assessed, two from Pitt (N=10 and 22) and one from PSU (N=37). PSU results were normalized against 18S, Pitt against CTRC. From each of these three data sets, mean gene expression per sample was regressed against allele count to obtain an estimated slope, standard error, and z-score. We then calculated an overall z-score as a weighted average of the individual z-scores, with weights determined by sample size.

Antibodies:

Antibodies against claudin proteins (Invitrogen) were assessed using Western blot for mouse anti-claudin-2 (Catalog No. 32-5600), mouse anti-claudin-4 (Catalog No. 32-9400), and mouse alpha-tubulin antibody (Catalog no. AA12.1 The Developmental Studies Hybridoma Bank at the University of Iowa, http://dshb.biology.uiowa.edu/Antibody-list). Immunohistochemistry was performed using monoclonal antibodies for claudin-2 (Catalog #32-5600, 1:1,000 dilution). Immunoflourescence was performed using mouse anti-claudin-2 (Catalog No. 32-5600) and goat anti-human CD68 (Catalog #sc-7082, Santa Cruz Biotechnology Inc.). The secondary antibodies for Immunofluorescence were goat anti-mouse CY3 and anti goat Cy5 from Jackson Immunoresearch.

SDS-PAGE and WESTERN Blotting:

Protein homogenates for Western blotting were obtained from snap-frozen tissue that was homogenized and sonicated in lysis buffer supplemented with protease inhibitors. Protein concentration was determined by the Bradford method using a kit from Bio-Rad. Proteins were separated on 12% SDS-PAGE[42] followed by transfer to polyvinylidene difluoride (PVDF) membranes[43], for Western blotting[44]. Immunodetection of bound antibodies on PVDF membrane was performed using ECL reagents (Amersham Biosciences). All procedures were carried out according to manufacturer instructions.

Immunohistochemistry:

Standard automated immunohistochemistry was performed for claudin 2 (antibodies listed above) on formalin-fixed, paraffin-embedded, 5 micron-thick tissue sections. Following deparaffinization in xylene and rehydration in ethanol, antigen retrieval was performed using EDTA pH8 buffer. The Dako Autostainer Plus was used; the slides were incubated for 30 minutes with the primary antibodies, followed by incubation with the secondary reagent (Mach 2 Mouse HRP Polymer from Biocare Medical) for 30 minutes. The chromogen was developed (Dako DAB+) for 10 minutes. The immunohistochemical stains were reviewed by one of the authors (A.M.K.). Cytoplasmic, granular, and membranous staining, predominantly in the lateral cell membranes, were graded on an intensity scale of 0-4 (0, negative; 1, weak; 2, moderate; 3, strong). The staining intensity was very patchy from lobule to lobule in most cases.

Immunofluorescence:

Cryostat sections (5 micron) of pancreas were washed 3 times with phosphate-buffered saline (PBS), followed by 3 washes with solution of 0.5% BSA in PBS. Sections were blocked with 2% BSA solution for 30 minutes. The slides were incubated for 1 hour at room temperature with primary antibody for claudin-2 1:100 and goat anti-human CD68 in 0.5% BSA solution. Slides were washed 3 times with BSA solution and incubated for 1 hour at 20° C. with 1:500 dilution anti-goat CY5 and 1:1000 dilution goat anti-mouse CY3 secondary antibodies in BSA solution. Nuclei were stained with Hoeschts dye (bisbenzamide 1 mg/100 ml water) for 30 seconds. After 3 rinses with PBS, sections were cover slipped with Gelvatol mounting media. Fluorescent images were captured with an Olympus Fluoview 1000 confocal microscope (software version 1.7a). The Cy5 signal (CD68) was pseudocolored as green to show colocalization with the red Claudin signal as yellow.

REFERENCES

1. Etemad, B. & Whitcomb, D. C. Chronic pancreatitis: Diagnosis, classification, and new genetic developments. *Gastroenterology* 120, 682-707 (2001).
2. Chen, J. M. & Ferec, C. Chronic pancreatitis: genetics and pathogenesis. *Annu Rev Genomics Hum Genet* 10, 63-87 (2009).
3. Witt, H., Apte, M. V., Keim, V. & Wilson, J. S. Chronic pancreatitis: challenges and advances in pathogenesis, genetics, diagnosis, and therapy. *Gastroenterology* 132, 1557-73 (2007).
4. Whitcomb, D. C. What is personalized medicine—what does it replace? *Nat Rev Gastroenterol Hepatol* (2012).
5. Whitcomb, D. C. et al. Multicenter approach to recurrent acute and chronic pancreatitis in the United States: the North American Pancreatitis Study 2 (NAPS2). *Pancreatology* 8, 520-31 (2008).
6. Yadav, D. & Whitcomb, D. C. The role of alcohol and smoking in pancreatitis. *Nat Rev Gastroenterol Hepatol* 7, 131-45 (2010).
7. Skol, A. D., Scott, L. J., Abecasis, G. R. & Boehnke, M. Joint analysis is more efficient than replication-based analysis for two-stage genome-wide association studies. *Nature genetics* 38, 209-13 (2006).
8. Whitcomb, D. C. et al. Hereditary pancreatitis is caused by a mutation in the cationic trypsinogen gene. *Nature Genetics* 14, 141-5 (1996).
9. Masson, E. et al. Trypsinogen copy number mutations in patients with idiopathic chronic pancreatitis. *Clin Gastroenterol Hepatol* 6, 82-8 (2008).
10. Larusch, J., Barmada, M. M., Solomon, S. & Whitcomb, D. C. Whole exome sequencing identifies multiple, complex etiologies in an idiopathic hereditary pancreatitis kindred. *JOP: Journal of the pancreas* 13, 258-62 (2012).
11. Witt, H. et al. A degradation-sensitive anionic trypsinogen (PRSS2) variant protects against chronic pancreatitis. *Nat Genet* 38, 668-73 (2006).
12. A map of human genome variation from population-scale sequencing. *Nature* 467, 1061-73 (2010).
13. Johnson, A. D. et al. SNAP: a web-based tool for identification and annotation of proxy SNPs using HapMap. *Bioinformatics* 24, 293 8-9 (2008).
14. Dawra, R. et al. Intra-acinar trypsinogen activation mediates early stages of pancreatic injury but not inflammation in mice with acute pancreatitis. *Gastroenterology* 141, 2210-2217 e2 (2011).
15. Van Itallie, C. M. et al. The density of small tight junction pores varies among cell types and is increased by expression of claudin-2. *Journal of cell science* 121, 298-305 (2008).
16. Amasheh, S. et al. Claudin-2 expression induces cation-selective channels in tight junctions of epithelial cells. *Journal of cell science* 115, 4969-76 (2002).
17. Lee, J. H. et al. Immunohistochemical analysis of claudin expression in pancreatic cystic tumors. *Oncology reports* 25, 971-8 (2011).
18. Aung, P. P. et al. Differential expression of claudin-2 in normal human tissues and gastrointestinal carcinomas. *Virchows Archiv: an international journal of pathology* 448, 428-34 (2006).
19. Sakaguchi, T. et al. Cloning of the human claudin-2 5'-flanking region revealed a TATA-less promoter with conserved binding sites in mouse and human for caudal-related homeodomain proteins and hepatocyte nuclear factor-1alpha. *The Journal of biological chemistry* 277, 21361-70 (2002).
20. Mankertz, J. et al. TNFalpha up-regulates claudin-2 expression in epithelial HT-29/B6 cells via phosphatidylinositol-3-kinase signaling. *Cell and tissue research* 336, 67-77 (2009).
21. Suzuki, T., Yoshinaga, N. & Tanabe, S. Interleukin-6 (IL-6) regulates claudin-2 expression and tight junction permeability in intestinal epithelium. *The Journal of biological chemistry* 286, 31263-71 (2011).
22. Mankertz, J. et al. Functional crosstalk between Wnt signaling and Cdx-related transcriptional activation in the regulation of the claudin-2 promoter activity. *Biochemical and biophysical research communications* 314, 1001-7 (2004).
23. Merilainen, S. et al. Acute edematous and necrotic pancreatitis in a porcine model. *Scandinavian journal of gastroenterology* 43, 1259-68 (2008).
24. Liggins, A. P. et al. MORC4, a novel member of the MORC family, is highly expressed in a subset of diffuse large B-cell lymphomas. *British journal of haematology* 138, 479-86 (2007).
25. Van den Bossche, J. et al. Claudin-1, claudin-2 and claudin-11 genes differentially associate with distinct types of anti-inflammatory macrophages in vitro and with parasite- and tumor-elicited macrophages in vivo. *Scandinavian journal of immunology* (2012).
26. Ammann, R. W., Akovbiantz, A., Largiader, F. & Schueler, G. Course and outcome of chronic pancreatitis. Longitudinal study of a mixed medical-surgical series of 245 patients. *Gastroenterology* 86, 820-8 (1984).
27. Marks, I. N., Bank, S. & Louw, J. H. Chronic pancreatitis in the Western Cape. *Digestion* 9, 447-53. (1973).
28. Robles-Diaz, G., Vargas, F., Uscanga, L. & Fernandez-del Castillo, C. Chronic pancreatitis in Mexico City. *Pancreas* 5, 479-83 (1990).
29. Irving, H. M., Samokhvalov, A. V. & Rehm, J. Alcohol as a risk factor for pancreatitis. A systematic review and meta-analysis. *JOP* 10, 387-92 (2009).
30. Yadav, D., Eigenbrodt, M. L., Briggs, M. J., Williams, D. K. & Wiseman, E. J. Pancreatitis: prevalence and risk factors among male veterans in a detoxification program. *Pancreas* 34, 390-8 (2007).

31. Yadav, D. et al. Alcohol consumption, cigarette smoking, and the risk of recurrent acute and chronic pancreatitis. *Arch Intern Med* 169, 1035-45 (2009).
32. Bacanu, S. A., Devlin, B. & Roeder, K. The power of genomic control. *American journal of human genetics* 66, 1933-44 (2000).
33. Naj, A. C. et al. Common variants at MS4A4/MS4A6E, CD2AP, CD33 and EPHA1 are associated with late-onset Alzheimer's disease. *Nature genetics* 43, 436-41 (2011).
34. Hamza, T. H. et al. Genome-wide gene-environment study identifies glutamate receptor gene GRIN2A as a Parkinson's disease modifier gene via interaction with coffee. *PLoS genetics* 7, e1002237 (2011).
35. Purcell, S. et al. PLINK: a tool set for whole-genome association and population-based linkage analyses. *American journal of human genetics* 81, 559-75 (2007).
36. Yang, J., Lee, S. H., Goddard, M. E. & Visscher, P. M. GCTA: a tool for genome-wide complex trait analysis. *American journal of human genetics* 88, 76-82 (2011).
37. Klei, L., Kent, B. P., Melhem, N., Devlin, B. & Roeder, K. GemTools: a fast and efficient approach to estimating genetic ancestry. (2011).
38. Price, A. L. et al. Principal components analysis corrects for stratification in genome-wide association studies. *Nature genetics* 38, 904-9 (2006).
39. Clayton, D. G. Sex chromosomes and genetic association studies. *Genome medicine* 1, 110 (2009).
40. Zheng, G., Joo, J., Zhang, C. & Geller, N. L. Testing association for markers on the X chromosome. *Genetic epidemiology* 31, 834-43 (2007).
41. Pfutzer, R. H. et al. SPINK1/PSTI polymorphisms act as disease modifiers in familial and idiopathic chronic pancreatitis. *Gastroenterology* 119, 615-23 (2000).
42. Laemmli, U. K. Cleavage of structural proteins during the assembly of the head of bacteriophage T4. *Nature* 227, 680-5 (1970).
43. Towbin, H., Staehelin, T. & Gordon, J. Electrophoretic transfer of proteins from polyacrylamide gels to nitrocellulose sheets: procedure and some applications. *Proceedings of the National Academy of Sciences of the United States of America* 76, 4350-4 (1979).
44. Burnette, W. N. "Western blotting": electrophoretic transfer of proteins from sodium dodecyl sulfate—polyacrylamide gels to unmodified nitrocellulose and radiographic detection with antibody and radioiodinated protein A. *Analytical biochemistry* 112, 195-203 (1981).
45. Szmola, R. & Sahin-Toth, M. Chymotrypsin C (caldecrin) promotes degradation of human cationic trypsin: identity with Rinderknecht's enzyme Y. Proc Natl Acad Sci USA 104, 11227-32 (2007).
46. Rosendahl, J. et al. Chymotrypsin C (CTRC) variants that diminish activity or secretion are associated with chronic pancreatitis. Nat Genet 40, 78-82 (2008).
47. Lasson, A., Borgstrom, A. & Ohlsson, K. Elevated pancreatic secretory trypsin inhibitor levels during severe inflammatory disease, renal insufficiency, and after various surgical procedures. Scand J Gastroenterol 21, 1275-80 (1986).
48. Ogawa, M. Pancreatic secretory trypsin inhibitor as an acute phase reactant. Clin Biochem 21, 19-25 (1988).
49. Schneider, A. et al. Combined Bicarbonate Conductance-Impairing Variants in CFTR and SPINK1 Variants Are Associated With Chronic Pancreatitis in Patients Without Cystic Fibrosis. Gastroenterology 140, 162-71 (2011).
50. Racz, G. Z. et al. Extracellular calcium sensing receptor in human pancreatic cells. Gut 51, 705-11 (2002).
51. Dawra, R. et al. Intra-acinar trypsinogen activation mediates early stages of pancreatic injury but not inflammation in mice with acute pancreatitis. Gastroenterology 141, 2210-2217 e2 (2011).
52. Amasheh, S. et al. Claudin-2 expression induces cation-selective channels in tight junctions of epithelial cells. Journal of cell science 115, 4969-76 (2002).
53. Angelow, S., Ahlstrom, R. & Yu, A. S. Biology of claudins. American journal of physiology. Renal physiology 295, F867-76 (2008).
54. Laurila, J. J. et al. Tight junction proteins in gallbladder epithelium: different expression in acute acalculous and calculous cholecystitis. The journal of histochemistry and cytochemistry: official journal of the Histochemistry Society 55, 567-73 (2007).
55. Mankertz, J. et al. TNFalpha up-regulates claudin-2 expression in epithelial HT-29/B6 cells via phosphatidylinositol-3-kinase signaling. Cell and tissue research 336, 67-77 (2009).
56. Suzuki, T., Yoshinaga, N. & Tanabe, S. Interleukin-6 (IL-6) regulates claudin-2 expression and tight junction permeability in intestinal epithelium. The Journal of biological chemistry 286, 31263-71 (2011).
57. Schmid-Kotsas, A. et al. Lipopolysaccharide-activated macrophages stimulate the synthesis of collagen type I and C-fibronectin in cultured pancreatic stellate cells. The American journal of pathology 155, 1749-58 (1999).
58. Van den Bossche, J. et al. Claudin-1, claudin-2 and claudin-11 genes differentially associate with distinct types of anti-inflammatory macrophages in vitro and with parasite- and tumour-elicited macrophages in vivo. Scandinavian journal of immunology 75, 588-98 (2012).
59. Whitcomb, D. C. et al. Multicenter approach to recurrent acute and chronic pancreatitis in the United States: the North American Pancreatitis Study 2 (NAPS2). Pancreatology 8, 520-31 (2008).
60. Whitcomb, D. C. et al. Angiopoietin-2, a Regulator of Vascular Permeability in Inflammation, Is Associated With Persistent Organ Failure in Patients With Acute Pancreatitis From the United States and Germany. Am J Gastroenterol 105, 2287-92 (2010).
61. Brand, R. E. et al. Serum Biomarker Panels for the Detection of Pancreatic Cancer. Clin Cancer Res 17, 805-816 (2011).
62. Applebaum-Shapiro, S. E. et al. Hereditary Pancreatitis in North America: The Pittsburgh—Midwest Multi-Center Pancreatic Study Group Study. *Pancreatology* 1, 439-443 (2001).
63. Naj, A. C. et al. Common variants at MS4A4/MS4A6E, CD2AP, CD33 and EPHA1 are associated with late-onset Alzheimer's disease. Nature genetics 43, 436-41 (2011).
64. Hamza, T. H. et al. Genome-wide gene-environment study identifies glutamate receptor gene GRIN2A as a Parkinson's disease modifier gene via interaction with coffee. PLoS genetics 7, e1002237 (2011).
65. Aung, P. P. et al. Differential expression of claudin-2 in normal human tissues and gastrointestinal carcinomas. Virchows Archiv: an international journal of pathology 448, 428-34 (2006).
66. Lee, J. H. et al. Immunohistochemical analysis of claudin expression in pancreatic cystic tumors. Oncology reports 25, 971-8 (2011).

The invention claimed is:

1. A method for treating pancreatitis in a human subject in need thereof comprising:
   (a) testing a sample from the subject for the presence of a rs12688220 T allele, a rs7057398 T allele, and a rs10273639 C allele,
   wherein the presence of an allele is detected by an assay selected from the group consisting of polymerase chain reaction, quantitative polymerase chain reaction, nucleic acid sequencing, and nucleic acid microarray analysis; and
   (b) where the rs12688220 T allele is present in the sample, administering a treatment for pancreatitis to the subject selected from the group consisting of cholecystectomy, biliary sphincterotomy, administration of an antibiotic, administration of carbapenem, administration of a therapeutic enzyme, surgery, distal pancreatectomy, celiac nerve block, percutaneous drainage, and combinations thereof.

2. The method of claim 1, further comprising, prior to treatment administration, a diagnostic procedure selected from the group consisting of a biochemical assay for iso-amylase, lipase, trypsin, elastase, and/or secretin level in a sample from the subject, quantitative measurement of fecal fat, measurement of plasma cholecystokinin (CCK), assay for pancreatic exocrine function, radiological testing, transabdominal ultrasound, CT scanning, magnetic resonance cholangiopancreatography (MRCP), endoscopic diagnosis assay, and combination thereof.

3. A method for treating pancreatitis in a human subject in need thereof comprising:
(a) testing a sample from the subject for the presence of a rs12688220 T allele, a rs7057398 T allele, and a rs10273639 C allele,
wherein the presence of an allele is detected by an assay selected from the group consisting of polymerase chain reaction, quantitative polymerase chain reaction, nucleic acid sequencing, and nucleic acid microarray analysis; and
(b) where the rs7057398 T allele is present in the sample,
administering a treatment for pancreatitis to the subject selected from the group consisting of cholecystectomy, biliary sphincterotomy, administration of an antibiotic, administration of carbapenem, administration of a therapeutic enzyme, surgery, distal pancreatectomy, celiac nerve block, percutaneous drainage, and combinations thereof.

4. The method of claim 3, further comprising, prior to treatment administration, a diagnostic procedure selected from the group consisting of a biochemical assay for iso-amylase, lipase, trypsin, elastase, and/or secretin level in a sample from the subject, quantitative measurement of fecal fat, measurement of plasma cholecystokinin (CCK), assay for pancreatic exocrine function, radiological testing, transabdominal ultrasound, CT scanning, magnetic resonance cholangiopancreatography (MRCP), endoscopic diagnosis assay, and combination thereof.

5. A method for treating pancreatitis in a human subject in need thereof comprising:
(a) testing a sample from the subject for the presence of a rs12688220 T allele, a rs7057398 T allele, and a rs10273639 C allele,
wherein the presence of an allele is detected by an assay selected from the group consisting of polymerase chain reaction, quantitative polymerase chain reaction, nucleic acid sequencing, and nucleic acid microarray analysis; and
(b) where the rs10273639 C allele is present in the sample,
administering a treatment for pancreatitis to the subject selected from the group consisting of cholecystectomy, biliary sphincterotomy, administration of an antibiotic, administration of carbapenem, administration of a therapeutic enzyme, surgery, distal pancreatectomy, celiac nerve block, percutaneous drainage, and combinations thereof.

6. The method of claim 5, further comprising, prior to treatment administration, a diagnostic procedure selected from the group consisting of a biochemical assay for iso-amylase, lipase, trypsin, elastase, and/or secretin level in a sample from the subject, quantitative measurement of fecal fat, measurement of plasma cholecystokinin (CCK), assay for pancreatic exocrine function, radiological testing, transabdominal ultrasound, CT scanning, magnetic resonance cholangiopancreatography (MRCP), endoscopic diagnosis assay, and combination thereof.

7. The method of claim 1, comprising determining the presence of nucleic acid comprising SEQ ID NO:2 in the sample.

\* \* \* \* \*

SEQUENCE LISTING

<160> NUMBER OF SEQ ID NOS: 6

<210> SEQ ID NO 1
<211> LENGTH: 11
<212> TYPE: DNA
<213> ORGANISM: Homo sapiens

<400> SEQUENCE: 1
tttaccccca t                                                                11

<210> SEQ ID NO 2
<211> LENGTH: 11
<212> TYPE: DNA
<213> ORGANISM: Homo sapiens

<400> SEQUENCE: 2
tttactccca t                                                                11

<210> SEQ ID NO 3
<211> LENGTH: 11
<212> TYPE: DNA
<213> ORGANISM: Homo sapiens

<400> SEQUENCE: 3
gcctctagaa a                                                                11

<210> SEQ ID NO 4
<211> LENGTH: 11
<212> TYPE: DNA
<213> ORGANISM: Homo sapiens

<400> SEQUENCE: 4
gcctccagaa a                                                                11

<210> SEQ ID NO 5
<211> LENGTH: 11
<212> TYPE: DNA
<213> ORGANISM: Homo sapiens

<400> SEQUENCE: 5
accaacgctt g                                                                11

<210> SEQ ID NO 6
<211> LENGTH: 11
<212> TYPE: DNA
<213> ORGANISM: Homo sapiens

<400> SEQUENCE: 6
accaatgctt g                                                                11